(12) United States Patent
Olek

(10) Patent No.: US 11,319,581 B2
(45) Date of Patent: May 3, 2022

(54) METHOD FOR EPIGENETIC IMMUNE CELL COUNTING

(71) Applicant: Epiontis GmbH, Berlin (DE)

(72) Inventor: Sven Olek, Berlin (DE)

(73) Assignee: Precision for Medicine GmbH, Berlin (DE)

(*) Notice: Subject to any disclaimer, the term of this patent is extended or adjusted under 35 U.S.C. 154(b) by 179 days.

(21) Appl. No.: 16/484,246

(22) PCT Filed: Feb. 8, 2018

(86) PCT No.: PCT/EP2018/053206
§ 371 (c)(1),
(2) Date: Aug. 7, 2019

(87) PCT Pub. No.: WO2018/146209
PCT Pub. Date: Aug. 16, 2018

(65) Prior Publication Data
US 2019/0390263 A1 Dec. 26, 2019

(30) Foreign Application Priority Data
Feb. 9, 2017 (EP) .................................. 17155496

(51) Int. Cl.
*C12Q 1/68* (2018.01)
*C12Q 1/6851* (2018.01)
*C12Q 1/6881* (2018.01)

(52) U.S. Cl.
CPC ......... *C12Q 1/6851* (2013.01); *C12Q 1/6881* (2013.01); *C12Q 2600/154* (2013.01)

(58) Field of Classification Search
CPC ...................................................... C12Q 1/68
USPC ......................................................... 435/6.1
See application file for complete search history.

(56) References Cited

FOREIGN PATENT DOCUMENTS

| EP | 2199411 A1 * | 6/2010 | ........... C12Q 1/6881 |
| EP | 2199411 A1 | 6/2010 | |
| WO | WO-2014170497 A2 * | 10/2014 | ........... C12Q 1/6851 |
| WO | WO2014170497 A2 | 10/2014 | |

OTHER PUBLICATIONS

Adan A et al Flow cytometry: basic principles and applications. Critical Reviews in Biotechnology, 37(2): 163-176 (2017).
Auletta JJ and Lazarus HM, Immune restoration following hematopoietic stem cell transplantation: an evolving target. Bone Marrow Transplantation, 35:835-857 (2005).
Baron U, et al., DNA demethylation in the human FOXP3 locus discriminates regulatory T cells from activated FOXP3 (+) conventional T cells. European Journal of Immunology, vol. 37 (9) :2378-2389 (Sep. 2007).
Boldt A, Borte S, Fricke S, Kentouche K, Emmrich F, Borte M, Kahlenberg F, Sack U, Eight-color immunophenotyping of T-, B-, and NK-cell subpopulations for characterization of chronic immunodeficiencies, Cytometry B Clin Cytom., 86(3):191-206 (2014).

(Continued)

*Primary Examiner* — Aaron A Priest

(57) ABSTRACT

The present invention relates to improved methods for epigenetic blood and immune cell counting, and respective uses and kits.

9 Claims, 9 Drawing Sheets

(56) References Cited

OTHER PUBLICATIONS

Figure 1:
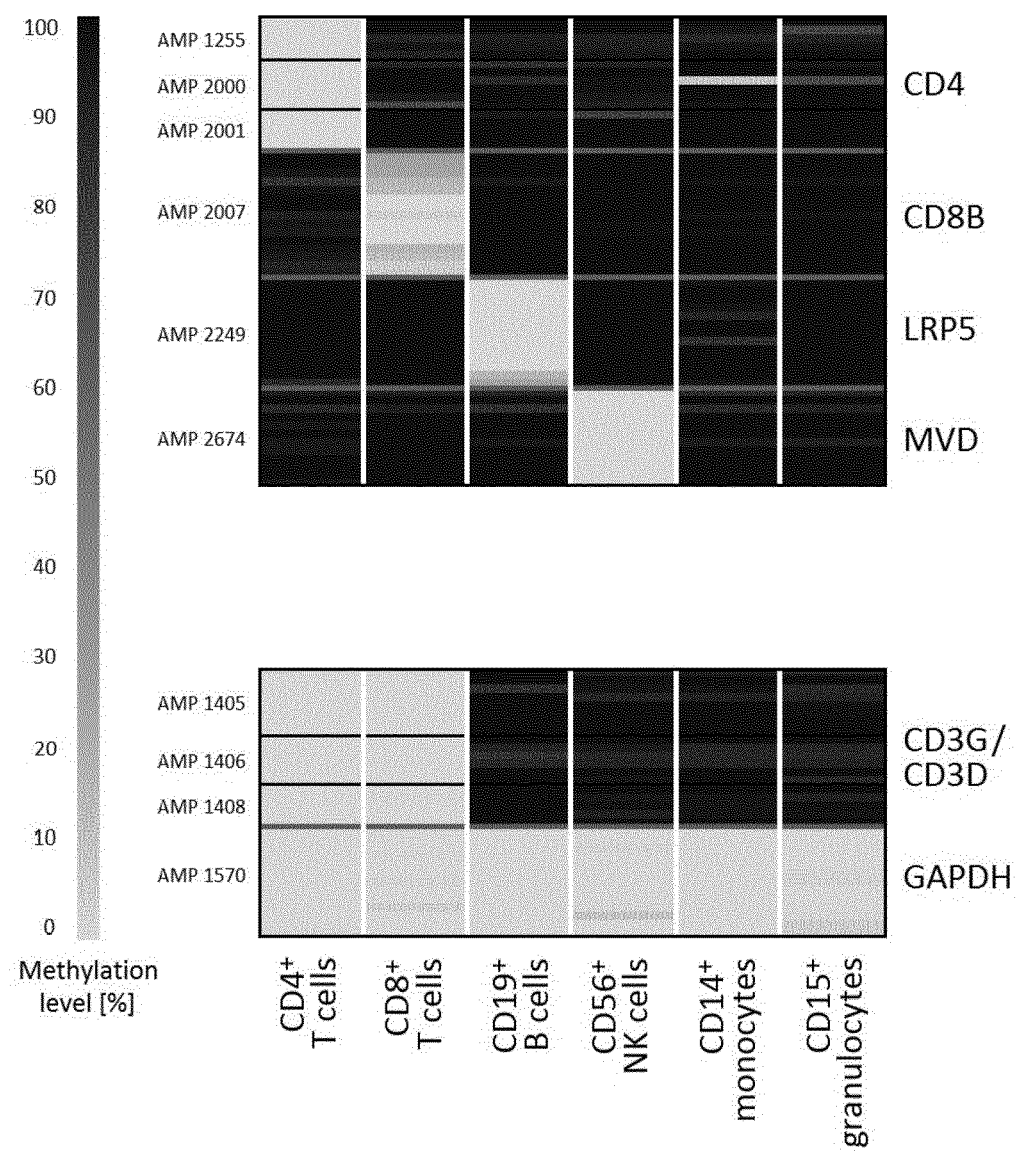

Chen D et al., Differential reactivity of the rat S100A4(p9Ka) gene to sodium bisulfite is associated with differential Tevels of the S100A4 (p9Ka) mRNA in rat mammary epithelial cells. J Biol Chem., 274(4):2483-91 (1999).
De Jonge, HJM et al., Evidence based selection of housekeeping genes. PLoS One 2(9):e898 (2007).
European Aids Clinical Society, European Guidelines for treatment of HIV-positive adults in Europe (2015) (Version 8.0; Jun. 2016).
Giavarina D., Understanding Bland Altman analysis. Biochemia Medica. 25(2):141-51 (2015).
Harrison J, Stirzaker C, Clark SJCytosines adjacent to methylated CpG sites can be partially resistant to conversion in genomic bisulfite sequencing leading to methylation artifacts. Anal Biochem. 264(1):129-32 (1998).
Herzenberg LA et al., Interpreting flow cytometry data. Nature Immunolog., vol. 7(7):681-685 (Jul. 2006).
International Human Genome Sequencing Consortium, Initial sequencing and analysis of the human genome. Nature, vol. 409: 860-921 (Feb. 15, 2001).
Israeli M, Klein T, Herscovici C, Ram R, Shpilberg O, Sredni B and Yeshurun M. Cellular immune function monitoring after allogeneic haematopoietic cell transplantation: evaluation of a new assay. Clinical and Experimental Immunology, vol. 172(3): 475-482 (2013).
Kverneland AH et al. Age and gender leucocytes variances and references values generated using the standardized ONE-Invention protocol. Cytometry Part A. / vol. 89(6):543-64 (2016).
Lee JW et al., Fit-for-purpose method development and validation for successful biomarker measurement. Pharmacetical Research, vol. 23(2):312-28 (2006).
Lewin J, et al. Quantitative DNA methylation analysis based on four dye trace data from direct sequencing of PCR amplificates. Bioinformatics, vol. 20:3005-12 (2004).
Maecker HT et al. (Standardizing immunophenotyping for the Human Immunology Project. Nat Rev Immunol. 12(3):191-200 (2012).
Maecker HT, McCoy JP Jr; FOCIS Human Immunophenotyping Consortium, Amos M, et al., A model for harmonizing flow cytometry in clinical trials. Nat Immunol, 11(11):975-8 (Nov. 2010).
McHugh, Mary L., Interrater reliability: the kappa statistic. Biochemica Medica (Zagreb) 22(3):276-282 (Oct. 2012).
Moore, DM et al., CD4 percentage is an independent predictor of survival in patients starting antiretroviral therapy with absolute CD4 cell counts between 200 and 350 cells/microL. HIV Med 7:383-388 (2006).
Nebe, CT et al., Messunsicherheit und Qualitatssicherung im Bereich der Immunphanotypisierung der Lymphozytensubpopulationen im peripheren Blut. J Lab Med 37(5):233-250 (2013)—English Abstract Attached to Article.
Shah Nina N et al., Hematopoietic Stem Cell Transplantation for Multiple Myeloma: Guidelines from the American Society for Blood and Marrow Transplantation. Biol Blood Marrow Transplant, vol. 21, Issue 7:1155-66 (Jul. 2015 ).
Read SJ, Recovery efficiencies of nucleic acid extraction kits as measured by quantitative LightCyclerTM PCR. Molecular Pathology, 54(2): 86-90 (Apr. 2001).
Rodriguez, W.R. et al, A microchip CD4 counting method for HIV monitoring in resource-poor settings, PLoS Med 2(7): e182-e182 (2005).
Sehouli J, et al., Epigenetic quantification of tumor-infiltrating T-lymphocytes, Epigenetics 6:236-46 (Feb. 2011).
Slatter Mary A., Cant AJ Hematopoietic stem cell transplantation for primary immunodeficiency diseases. Annals of the New York Academy of Sciences, 1238:122-31 (Nov. 30, 2011).
Thoma et al., Peripheral blood lymphocyte and monocyte recovery and survival in acute leukemia postmyeloablative allogeneic hematopoietic stem cell transplant. Biol Blood Marrow Transplant. 18(4):600-7 (Apr. 18, 2012).
Tsikas D, A proposal for comparing methods of quantitative analysis of endogenous compounds in biological systems by using the relative lower limit of quantification (rLLOQ). J Chromatogr B Analyt Technol Biomed Life Sci. 877(23):2244-51 (Aug. 2009).
Warnecke PM, Stirzaker C Detection and measurement of PCR bias in quantitative methylation analysis of bisulphite-treated DNA. Nucleic Acids Research, 25(21):4422-6 (1997).
Whitby L, et al., Current laboratory practices in flow cytometry for the enumeration of CD 4(+) T-lymphocyte subsets. Cytometry Part B: Clinical Cytometry, vol. 88(5):305-11 (2015).
WHO Consolidated guidelines on the use of antiretroviral drugs for treating and preventing HIV infection. Recommendations for a public health approach—Second edition (2016).
Wieczorek G, et al., Quantitative DNA methylation analysis of FOXP3 as a new method for counting regulatory T cells in peripheral blood and solid tissue. Cancer Research, 69:599-608 (Jan. 15, 2009).
Yu LM, Easterbrook PJ, Marshall T Relationship between CD4 count and CD4% in HIV-infected people. International Journal of Epidemiology, vol. 26(6):1367-72 (1997).

* cited by examiner

A)

B)

C)

METHOD FOR EPIGENETIC IMMUNE CELL COUNTING

CROSS-REFERENCE TO RELATED APPLICATIONS

This application is a 35 U.S.C. § 371 national phase application of International Patent Application No. PCT/EP2018/053206, filed Feb. 8, 2018, which claims priority to European Patent Application No. 17155496.7, filed Feb. 9, 2017, the entire disclosures of each of which are incorporated herein by reference in their entirety.

The present invention relates to improved methods for epigenetic blood and immune cell counting, and respective uses and kits.

BACKGROUND OF THE INVENTION

Deviation from the physiological balance of cellular immune system is indicative of various diseases and therefore constitutes an important measure for diagnosis and patient monitoring. The according measurements are currently best performed by flow cytometry (FCM), which provides both accuracy and flexibility with respect to the cell type to be determined (1). However and although hematology analyzers used in diagnostic laboratories are highly developed and logistic environments are extensively adapted to the required processes, this approach is limited in its applicability.

FCM-based cell counting requires fresh, anti-coagulated or well-preserved blood samples with intact leukocytes. Even with fresh samples, it is advisable to work quickly since time-to-analysis can influence the results with cell deterioration beginning in the initial hours after blood draw. Moreover, standardization of FCM remains a significant challenge due to biological, technical and operational variation (2,3,4,5) and completely standardized measurements have not yet been achieved (6, 7). The most critical challenge, however, is that not all medical applications warrant availability of fresh or well-conserved blood samples and flow cytometry cannot be applied in these cases.

For example, therapy decisions for HIV infected patients hinge on the patients' $CD4^+$ T helper cell count. At a frequency below 500 T helper cells per microliter, antiretroviral therapy is strongly recommended and becomes imperative at levels below 200 cells per microliter. In resource-poor countries, an appropriate diagnostic assessment is often hampered in rural areas where blood draw and measurement cannot be performed in close succession. As a result, treatment is frequently initiated based solely on HIV-related clinical symptoms, which can result in suboptimal outcomes (8, 9).

Another example is newborn screening. Guthrie cards from heel pricks are collected and used for the detection of severe, curable inborn defects. These cards cannot be used for flow cytometric analysis and T-cell receptor excision circles (TREC) are used for PID-screening instead. TREC analysis preferentially detects recent thymic emigrants, the predominant T-cell subtype in the periphery of newborns. However, this technology is limited to T- and, more recently also B-(KREC), cells but is not fit for differential analysis, such as CD4 or CD8 subpopulations and also fails to detect other cell types, such as NK cells. Therefore, TREC analysis in newborn analysis is exclusively used for initial screening. Differential diagnosis and patient monitoring prior to and upon the curative hematopoetic stem cell transplantation requires change of technology and is performed by flow cytometry.

In order to overcome diagnostic limitations and the associated technological switches, an improved means for immune status assessment would be valuable. It should robustly provide relative and absolute cell counts equally allowing the use of fresh, frozen or paper-spotted blood. Signals should be digital for each analyzed cell, i.e., indicating either one positive or negative value per cell rather than requiring arbitrarily defined thresholds for "positiveness". Such new method should also be performed in an automated, operator-independent manner and less dependent on the variability of reagents used, such as antibodies.

In a first aspect of the present invention, the above object is solved by a method for a quantitative methylation assay for blood immune cells, comprising the steps of
a) providing a defined volume of a sample of human blood comprising diploid genomic DNA of blood immune cells to be quantitated;
b) providing an in silico bisulfite-converted recombinant nucleic acid comprising at least one demethylation standard gene, and a sequence inversing all CpG dinucleotides to GpC of said at least one demethylation standard gene ("standard I");
c) providing a recombinant nucleic acid comprising the demethylated genomic sequence of said at least one demethylation standard gene of b), and of said a sequence inversing all CpG dinucleotides to GpC of said at least one demethylation standard gene of b) ("calibrator I");
d) providing a recombinant nucleic acid comprising the sequence inversing all CpG dinucleotides to GpC of said at least one demethylation standard gene of b) ("spiker I");
e) adding a defined amount of said recombinant nucleic acid of d) to said sample of a) ("spiking");
f) treating said diploid genomic DNA of the cells to be quantitated of a) and said recombinant nucleic acids of c) and d) with bisulfite to convert unmethylated cytosines into uracil;
g) amplifying of said nucleic acid molecules of a), b), c), and f) using suitable primer pairs to produce amplicons; and
h) identifying the blood immune cells (BIC) per volume of sample based on analyzing said amplicons.

In a second aspect of the present invention, the above object is solved by a method for a quantitative methylation assay for blood cells, comprising the steps of
a) providing a sample of human blood comprising diploid genomic DNA of blood cells to be quantitated;
b) providing an in silico bisulfite-converted recombinant nucleic acid comprising at least one demethylation standard gene, and at least one blood cell specific gene ("standard II");
c) providing a recombinant nucleic acid comprising the demethylated genomic sequence of said at least one demethylation standard gene of b), and of said at least one blood cell specific gene of b) ("calibrator II");
d) treating said diploid genomic DNA of the cells to be quantitated of a) and said recombinant nucleic acid of c) with bisulfite to convert unmethylated cytosines into uracil;
e) amplifying of said nucleic acid molecules of a), b), c), and d) using suitable primer pairs to produce amplicons; and f) identifying the percent of demethylation per all cells (DDC) based on analyzing said amplicons.

In a particularly preferred third aspect of the present invention, the above object is solved by a method for determining the absolute copy number of methylated genes of an immune cell type, comprising
   a) Performing the method according to the first aspect of the invention as above,
   b) Performing the method according to the second aspect of the invention as above, and
   c) Multiplying the BIC as identified with the DDC as identified.

The steps of the methods of the present invention can be performed in parallel or combined reaction vials, as shown in FIG. 2.

The present invention relates to the accurate quantification of methylation data. This involves several components and considerations:
   1. An internal standard, e.g. in silico converted plasmids.
   2. A (e.g.) GAPDH normaliser in contrast to the methylated variant of a specific gene.
   3. Thus, a comparison of all demethylated copies by the obligatory demethylated GAPDH with the specific (but present in the same number of copies) demethylated gene according to the quantification with 1.
   4. Nevertheless, the above does not allow a truly "absolute" quantification, since the in silico converted standard does not correspond to the biological sample (which is converted only in the reaction vial.
   5. Solving the problem at 4. based on adding and measuring a so-called GNoMs (Genomic Normaliser of Methylation), here, all original sequences are equimolarly included into a plasmid and then submitted to the overall process (bisulfite treatment and purification). Since they are present 1:1 a standard can be identified after the quantification using the standards in 1 showing the difference between in silico and in situ methylation. Using this factor, the methylation value of the measurements can be corrected, which improves the result considerably.
   6. Using a defined amount of a nucleic acid (plasmid) with a standard gene having inverted CG bases, furthermore, any loss of material during the process can be accounted for, which further improves the method.

In principle, quantitative real-time PCRs (qPCR) is such an approach accomplishing the characteristics when based on highly cell-type specific epigenetic (i.e., DNA methylation) markers (14, 15, 16). Technically, when DNA is treated with bisulfite, unmethylated CpG dinucleotides are converted to TpGs ("TpG-variant"), whereas methylated CpG-dinucleotides remain unaltered ("CpG-variant"). Thus, bisulfite conversion translates epigenetic marks into sequence information allowing discrimination between—and quantification of both—variants. qPCR assays are non-susceptible to loss of cell integrity in a blood sample, since its DNA is a very stable entity. Epigenetic cell quantification can be thus performed on fresh peripheral blood, dried blood spots or any other specimens without particular demands on their state of preservation. One can assume the existence of two copies of each CpG locus per cell and that each locus is exclusively either methylated or demethylated in a single given cell. In addition, the essential components required for qPCR are synthetically produced and standardization is relatively easy to achieve when compared with the manufacturing of biological substances like specific antibodies. However, as of today, the applicability of such epigenetic approach has not been demonstrated, probably due to the absence of well-defined cell type specific biomarkers and a lack of methods to implement definitive and absolute quantification. Definitive quantification requires reference standards directly representing the biological substrate (17). Absolute quantification poses difficulties in DNA-based techniques since the relation between leukocyte DNA and blood volume is not biologically fixed and DNA recovery from blood extraction is semi-quantitative.

Here, the inventors introduce a panel of epigenetic immune cell specific qPCR-based assays for quantification of the major leukocyte populations in human blood samples. The assays are based on DNA methylation marks specific for overall T cells, $CD4^+$ T cells, $CD8^+$ T cells, B-cells and NK cells. The cell number per microliter of blood constitutes the standard of care when fresh blood samples are available e.g., for the determination of CD4+T cells in HIV striken patients. Therefore, the inventors propose a novel system for definitive and absolute counting of immune cells based on their cell type-specific epigenetic signals. The assay concept and the individual biomarkers were analyzed for their equivalence to the gold standard FCM technology. However, when the volume of a given blood is not exactly defined, as is the case for dried blood samples, relative measurement is more accurate and should be employed. Hence and in order to achieve a wide measurement spectrum, here the inventors tested various diagnostic applications, aiming at the degree of agreement of absolute quantification by analysis of healthy donors and a cohort of HIV-positive patients, but the inventors also determined the diagnostic quality by identifying PID patients within a cohort of healthy newborns cohort from dried blood spots.

In a preferred embodiment of the method(s) according to the present invention, the method is integrated, and comprises
   a) providing a defined volume of a sample of human blood comprising diploid genomic DNA of blood cells to be quantitated;
   b) providing an in silico bisulfite-converted recombinant nucleic acid comprising a demethylation standard gene, a sequence inversing all CpG dinucleotides to GpC of said demethylation standard gene, and a blood cell specific gene;
   c) providing a recombinant nucleic acid comprising the demethylated genomic sequence of said demethylation standard gene of b), a sequence inversing all CpG dinucleotides to GpC of said demethylation standard gene, and said blood cell specific gene of b);
   d) providing a recombinant nucleic acid comprising the sequence inversing all CpG dinucleotides to GpC of said at least one demethylation standard gene of b);
   e) adding a defined amount of said recombinant nucleic acid of d) to said sample of a) ("spiking");
   f) treating said diploid genomic DNA of the cells to be quantitated of a) and said recombinant nucleic acids of c) and d) with bisulfite to convert unmethylated cytosines into uracil;
   g) amplifying of said nucleic acid molecules of a), b), c), and f) using suitable primer pairs to produce amplicons; and
   h) identifying the amount of blood cells per volume of sample based on analyzing said amplicons.

Preferably, the nucleic acids are plasmids, e.g. linearized plasmids, such as bacterial plasmids, e.g. pUC.

In this aspect of the method, the amplification is normalized using a first in silico bisulfite converted nucleic acid (plasmid), comprising a demethylation standard gene (e.g. GAPDH), an "artificial sequence" (the sequence inversing all CpG dinucleotides to GpC), as well as a blood cell specific gene (a "specific gene"). All three elements are equally present (equimolar) on said nucleic acid, and are in silico bisulfite converted. Therefore, the normalization curve and the corresponding calibration curves can be directly compared with the sample, and the relative cell count can be determined from the ratio of blood cell specific gene to demethylation standard gene. Nevertheless, the nucleic acid does not correspond to the "real" sequence, since each C is replaced by a T. A serial dilution and determination of each concentration with all genes as mentioned generated the calibration curve for the assay.

In order to improve the accuracy of the approach, a second nucleic acid (plasmid) is used comprising the demethylation standard gene (e.g. GAPDH), the "artificial sequence" (the sequence inversing all CpG dinucleotides to GpC), and the blood cell specific gene (a "specific gene"). Nevertheless, these sequences are NOT in silico bisulfite converted, and correspond to the genomic sequences (in as far as the have a genomic counterpart, see below)—and thus can only be used for measuring the amplification (e.g. qPCR) efficiency.

The reason for the second standard is two-fold. A) For a definitive quantification a standard is required that is identical as in the biological sample to be analyzed (this is also a regulatory requirement). In the first nucleic acid, nevertheless, a double stranded AT-rich sequence is compared with a single-stranded U-rich sequence. Only the "true" bisulfite conversion of the double stranded nucleic acid allows for this definitive comparison. Then, the quotient of bisulfite conversion of blood cell specific gene to demethylation standard gene, normalized using the first nucleic acid, gives a factor of the efficiency. The same holds true for a quotient based on the division of the bisulfite conversion of the sequence inversing all CpG dinucleotides to GpC by the bisulfite conversion of the demethylation standard gene.

Preferably, the "artificial sequence" (the sequence inversing all CpG dinucleotides to GpC) is a random sequence comprising C and CpG sequences (for bisulfite conversion) that does not occur in the human genome. In one embodiment, the artificial sequence is the exact sequence of the part of GAPDH that is amplified (amplicon) wherein the CpG sequences are inverted into GpC sequences. The "artificial sequence" is found on all three nucleic acids as described above, namely on the first one (in silico bisulfite converted), the second one (for bisulfite conversion), and—as the only analyzed sequence—on the third nucleic acid (in silico bisulfite converted).

The third nucleic acid is given in a defined amount into a defined amount of blood, and is then analyzed (e.g. purification, bisulfite treatment, second purification, desulfonation, specific amplification). Then, a normalization is performed against the first nucleic acid (how many copies were measured and given into the reaction), the efficiency is determined using a comparison with the second nucleic acid, and the (residual) copy number is determined using the third nucleic acid. Any losses are compared with a loss of genomic DNA that was subjected to the same procedure. The overall process allows for a precise definitive and absolute quantification of said DNA, and through this the cells in a blood sample, such as, for example, whole blood.

In one embodiment, the invention relates to an artificial sequence that is the exact sequence of the part of GAPDH that is amplified (amplicon) wherein the CpG sequences are inverted into GpC sequences as a tool when performing the method(s) of the present invention.

The composition of the cellular immune system holds valuable diagnostic information for various diseases. The standard technology for quantitative immune cell monitoring is flow cytometry. However, this method is limited to blood samples in which cell-integrity is retained. In clinical routine, this effectively restricts analysis to fresh blood samples as analytical substrate.

In order to widen the margin of use of diagnostic immune monitoring, the inventors implemented epigenetic qPCR systems for quantification of the major leukocyte populations. Upon determining immune cell type specific methylation marks, whole blood from 25 healthy donors, 97 HIV patients and 325 Guthrie cards from newborns including 25 cards from patients with primary immunodeficiencies (PID) were analyzed. Methodological concordance between flow cytometric and epigenetic data for B-, NK-, total T cells, T helper cells and cytotoxic T cells was determined and the ability of this new technique to identify quantitative immune cell deficiencies was challenged.

Data show that quantification via epigenetic qPCR assays and flow cytometry perform equivalently in healthy subjects and HIV patients according to Bland-Altman testing. Epigenetic quantification is applicable for relative and absolute frequencies of leukocyte subsets in fresh and frozen blood samples. In contrast to flow cytometry, immune cell analysis of Guthrie cards accurately identifies cases PID in newborns. Epigenetic quantification of immune cell populations performs with high equivalence to standard flow cytometry offering a wider range of possible applications, including analysis of dried blood spots possibly laying a path to blood counting of patients in remote areas or from newborns.

Preferred is the method according to the present invention, wherein said blood immune cell is selected from a leukocyte, a T-lymphocyte, a granulocyte, a monocyte, a B-lymphocyte and/or an NK-cell.

Preferred is the method according to the present invention, wherein said recombinant nucleic acid molecule is selected from a plasmid, a yeast artificial chromosome (YAC), human artificial chromosome (HAC), PI-derived artificial chromosome (PAC), a bacterial artificial chromosome (BAC), and a PCR-product.

Preferred is the method according to the present invention, wherein said demethylation standard gene is selected from a gene expressed in all cells to be detected, such as, for example, a housekeeping gene, such as, for example, GAPDH.

Preferred is the method according to the present invention, wherein said blood cell specific gene is selected from a gene expressed in all blood cells to be detected, such as, for example CD4.

Preferred is the method according to the present invention, wherein said blood sample is selected from peripheral, capillary or venous blood samples or subtractions thereof, such as, for example, peripheral blood monocytes, blood clots, and dried blood spots.

Preferred is the method according to the present invention, further comprising the step of concluding on the immune status of a mammal based on said quantification.

Another aspect of the invention relates to a diagnostic kit, comprising materials for performing the method according to the present invention, optionally with instructions for use. Preferred materials are the nucleic acid molecules, and/or a bisulphite reagent.

Another aspect of the invention relates to the use of the kit according to the invention for performing a method according to the invention.

Current immune cell monitoring requires fresh or well-conserved blood samples. Here, the inventors present an alternative technology for differential blood cell counting that allows calculation of relative and absolute cell numbers in fresh, formalin-fixed, frozen or dried blood samples.

Epigenetic qPCRs emerged as a promising tool without a need for intact cells or high standards of preservation. Data reporting the demethylation of the FOXP3 TSDR in regulatory T cells (14) showed the feasibility of such epigenetic cell counting.

In this invention, still open questions were addressed regarding a) the availability of feasible epigenetic markers for several important cell types, b) the normalization between various cell-type specific epigenetic qPCR systems, c) approaches to provide definitive quantification (17) for the epigenetic signals d) the quantification relative to a given blood volume and e) methodological agreement with the FCM gold standard technology to detect the according immune cell types.

Ideal DNA-methylation markers for cell-type identification are discriminative between the cell type of interest (near 0% methylation) and all other cell types (near 100% methylation). Here, markers for immune cell counting were investigated, initially applying the not fully quantitative method of bisulfite sequencing at putative discriminatory loci. These data show loci for all tested immune cell types tentatively fulfilling the criterion for ideal markers. Discriminatory CpG-dinucleotides were selected for qPCR assay development and tested on methylated and demethylated template variants. Efficient and quantitative amplification of target DNA was achieved without detecting background from non-target templates. qPCR assay performance was robust with low deviation in fresh or frozen blood.

For simultaneous testing of various different cell types in a heterogeneous sample, the use of locus-specific methylated (i.e., CpG) and demethylated (TpG) qPCRs is not optimal. Amplification efficiency varies for each qPCR system e.g., due to differing CpG-density, so that there is no biologically or technically stable parameter for all measurements (20). An invariably demethylated regulatory stretch of the housekeeping GAPDH (21) gene was used instead as a fixed denominator. In this way, each cell-type specific locus is counted relative to the number of loci demethylated in GAPDH, i.e., supposedly in all nucleated cells. Testing purified cell types at their specific epigenetic loci, however, showed that quantification with GAPDH as denominator deviates from quantification obtained with the locus-specifically methylated amplification systems. These deviations are dependent on the individual locus and amplification systems (22, 23) suggesting that normalization with a standard curve from in silico converted plasmid does not fully compensate for amplification differences in de facto bisulfite-converted DNA. Plasmid DNA is double-stranded and contains approximately 40% GC (24) outside of the templates for the epigenetic amplification. In contrast, bisulfite converted DNA is predominantly single-stranded with a significantly reduced GC content after amplification. Moreover, the latter has been exposed to harsh chemical treatment causing fragmentation which is not physically represented by in silico conversion of demethylated cytosine to thymine.

For compensation of this effect, a single plasmid molecule ("calibrator") containing the original demethylated genomic sequences of GAPDH and all immune cell-type specific marker genes was processed along with the biological samples. This calibrator provides for relative and equimolar quantification of bisulfite converted DNA via different qPCR systems. It does not replace the standard plasmid, however, since precise independent quantification along bisulfite conversion is challenging. Hence, in silico bisulfite-converted plasmid ("standard") continues to be used for copy number determination. The calibrator plasmid provided highly reproducible measurements throughout various experiments and compensates for the observed efficiency differences between GAPDH and the locus specific assays. Taken together, the parallel use of standard and calibrator plasmids renders the epigenetic qPCR into a method for definitive quantification (17) of demethylation in the respective loci relative to all (demethylated) GAPDH copies.

The data in FIG. 1 and Table 1 suggest that the analysis of differentially methylated loci is a powerful surrogate for detecting and quantifying defined immune cell types. In addition of cell type specificity, however, a direct proportional relation of cell type and DNA copy number needs to be experimentally established if cell counting by this means is intended. Such direct linear association may be impugned by residual DNA in thrombocytes, reticulocytes or by shifts between DNA-copies and cell numbers. Thus, cell quantification by epigenetic qPCR was orthogonally compared with FCM analysis. When using the definitive relative quantification introduced in this work, data for individual cell types and markers differed mildly with systemic biases ranging from −6% to +11%. Overall, however, high methodological agreement was observed between both technologies as whole and the selected individual markers.

With respect to routine clinical applications, relative cell type quantification is accepted by WHO in HIV-treatment guidelines, but medical reality demands cell counting per volume (25, 26). For epigenetic immune cell typing this poses a problem, since DNA recovery is not fully quantitative and a relation between DNA amount and blood volume is not biologically determined. Spiking a defined concentration of the inverse GAPDH variant ($GAP^{[GC]}$) into blood samples, however, allowed an approximated inference to the original DNA content prior to DNA extraction. Whereas different efficiencies of genomic DNA and plasmid DNA have been described (27), such difference might be significantly reduced after bisulfite treatment and resulting fragmentation. For evaluation of the spiking concept, epigenetic immune cell counting was paralleled with flow cytometry data from the same blood samples. With respect to bias and limits of agreements (28) the presented data show homogenous error distribution and smaller deviations than previously published methodological comparisons among different antibody-based methods (29). Hence, the inventors' data indicate that leukocyte subsets can be detected reliably by epigenetic immune cell counting and are almost comparable to FCM data.

An intrinsic challenge for quantitative diagnostic markers is their reliable performance outside the normal physiological range and from frugally conserved samples. For immune cell quantification, PIDs constitute such situation. Patients suffer from severe immune deficiencies, and quantitative cell counting via FCM is not feasible from dried blood cards for newborn screening.

In such case, comparison with the diagnostic performance of the gold standard method may best inform about the diagnostic power of the novel method. As direct method comparison is not feasible due to differing measurement parameters between TREC counting compared to cell quantification by FCM and/or epigenetic qPCR, such outcome comparison appears indispensable. Epigenetic immune cell counting reliably identifies all PID patients from dried blood spots, including XLA patients. In addition, it provides information on NK cell levels—an important hint for the underlying genetic defect, especially for ADA-SCID, since in these delayed onset form of SCID NK cells are—contrary to other forms of SCID—missing.

Taken together, the present invention shows that epigenetic cell counting provides precise and accurate means for immune monitoring, regardless if measured as continuous parameter in a percentage or absolute cell count or as categorical parameter. When detecting lower method agreement, as observed between the epigenetic and FCM markers for monocytes, this suggests that heterogeneity within a given cell population or ambiguous marker specificity influence agreement.

Altogether, this invention underlines the applicability of epigenetic immune monitoring as a valuable diagnostic way to immune diagnostics by providing a highly robust platform capable for analyzing samples from minute amounts of frugally conserved blood.

The present invention will now be explained further in the following examples and figures, nevertheless, without being limited thereto. For the purposes of the present invention, all references as cited herein are incorporated by reference in their entireties.

FIG. 1 shows the DNA methylation profile of marker genes in purified immune cell populations. The matrix shows cell type-specific DNA methylation patterns of seven marker genes and of the reference gene GAPDH. In the matrix, immune cell types are arranged in columns as indicated at the x-axis. Genes and corresponding amplicons (Amp) are indicated at the y-axis. Genes are separated by red lines with each row representing a single CpG site. Measured CpG methylation levels are color coded according to the color scale ranging from yellow (0% methylation) to blue (100% methylation).

FIG. 2 shows a schematic overview over the different quantification approaches for epigenetic cell counting. For all approaches, the inventors assumed a simplified 2-allels-to-1-cell relation. Each analyzed gene in this invention was autosomal (i.e., diploid), and has been shown to be demethylated in one specific cell type (in this scheme: the CD4 locus in $CD4^+$ T helper cells) whereas completely methylated in all other blood cell types. A) sketches the process for locus-specific relative percentage quantification. In blood samples with an unknown number (#) of demethylated and methylated diploid genomic DNA copies, a bisulfite conversion transfers the epigenetic methylation status into the primary sequence by exclusively converting demethylated Cytosins into Uracils. In CpG positions, methylated and demethylated cytosins occur depending on specific gene regulation. Converted Uracil-DNA is CpG-methylation status specific amplified by qPCR, whereby Uracil basepairs with adenosine resulting in an amplificate containing TpG dinucleotides at originally demethylated regions. qPCRs then allow counting of copy numbers as based on the calculation of serially diluted in silico converted plasmids by a linear interpolation (f-1) of the amplification results (f). Relative percentage methylation at the genomic locus is calculated by the interpolated copy number of originally demethylated copies at this locus divided by all copies at this locus, i.e., the methylated and demethylated ones. Conversion in the biological sample perturbs the integrity of the genomic DNA, whereas the plasmid represents the amplification product and not the substrate. The resulting difference in amplification efficiency is given by an unknown "conversion factor, (CF)". It is considered negligible when comparing amplification of two highly homologous sequences with few methylation-status dependent SNPs. For universal relative percentage qPCR (B), the same principles for epigenetic quantification are employed with regard to using an in silico converted plasmid standard, its interpolation and a cell type specific demethylated gene locus. Instead of the assessment of the cell specifically demethylated locus, the universally demethylated GAPDH locus representative for all cells is amplified. Using this as quantification reference all specific loci can be normalized to the overall genomic copy count. CF cannot be assumed to be similar in this case, as no homology between the different sequences is assumed. Relative demethylation per all cells is therefore disturbed by the presence of differing CFs. Compensating the influence of different conversion efficiencies, a calibrator plasmid is introduced as indicated in C). It contains equimolar genomics sequences of all relevant cell-specific loci and GAPDH. Interpolation of the amplification provides copy numbers for interference of differing conversion-specific efficiencies. The ratio of the differing copy numbers provides an efficiency factor (EF) that can be used to eliminate conversion related differences between standards and samples. Incorporating EF into (B) provides for definitive copy number quantification. D) For counting cells per volume of blood, a defined volume of blood is supplemented with known copy number of plasmid containing a synthetic, not natural DNA sequence (GAP-GC). Relative quantification using the in silico converted plasmid and calculation of EF operates as indicated above. Interpolating the starting amount of GAP-GC allows monitoring of DNA preparation, conversion and qPCR provides a good estimator for process efficacy. Calculation of the starting amount of blood cells therewith becomes possible.

Figure 3:
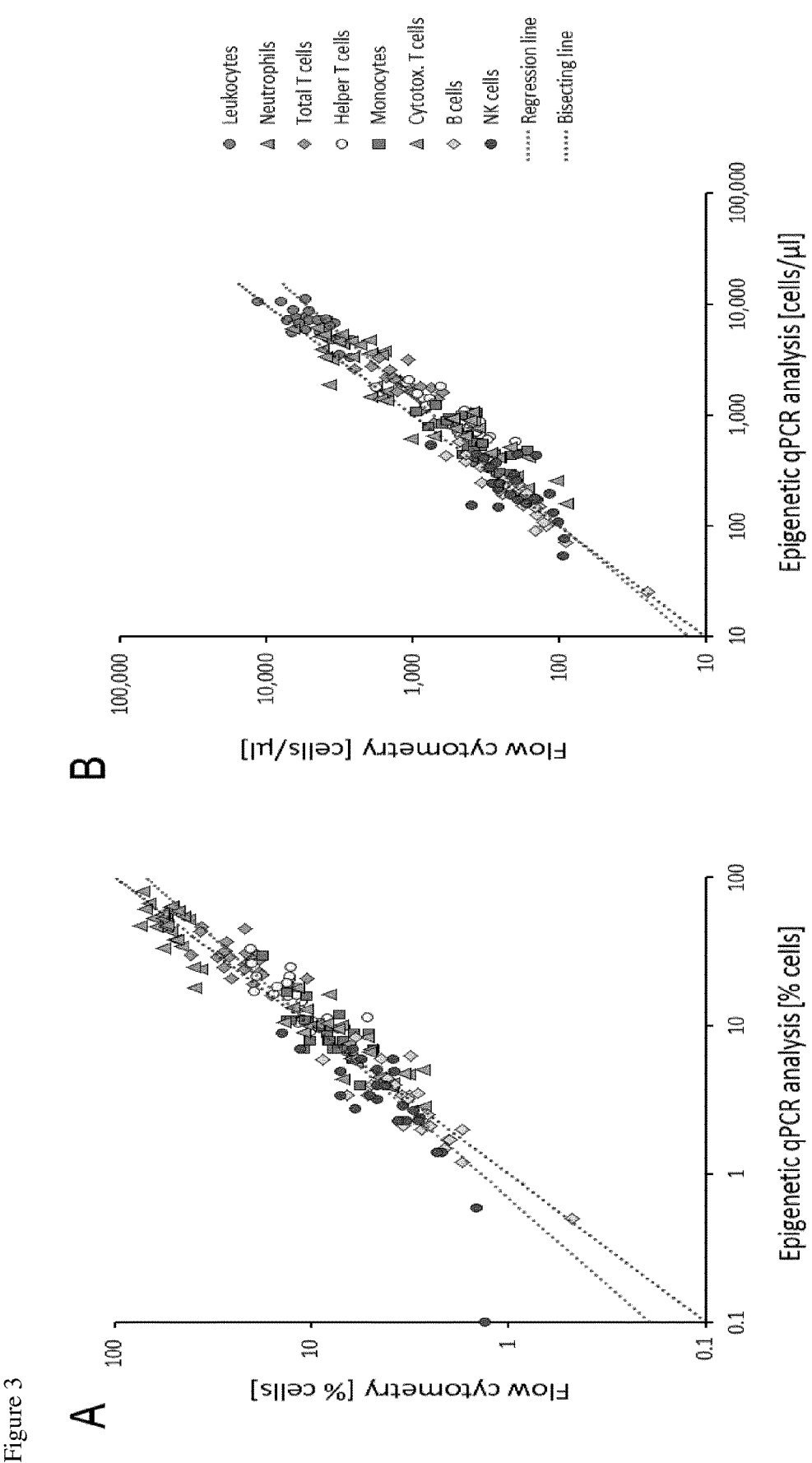

FIG. 3 shows the comparison of immune cell quantification by flow cytometry and epigenetic qPCR in blood from 25 healthy donors. Immune cells as measured via flow cytometry (y-axis) were scatter plotted over corresponding values determined via immune cell type specific epigenetic qPCR analysis (x-axis). A) shows relative immune cell counting where values are given in percent among total leukocytes. Linear Pearson correlation coefficients were r=0.95. B) displays absolute immune cell counting where values are expressed as cell number per µl of blood featuring a correlation of r=0.95. The red line represents the regression line computed from all data points, the black line indicates the bisectrix. Symbols in the right-hand legend illustrate the different individual immune cell populations.

Figure 4:
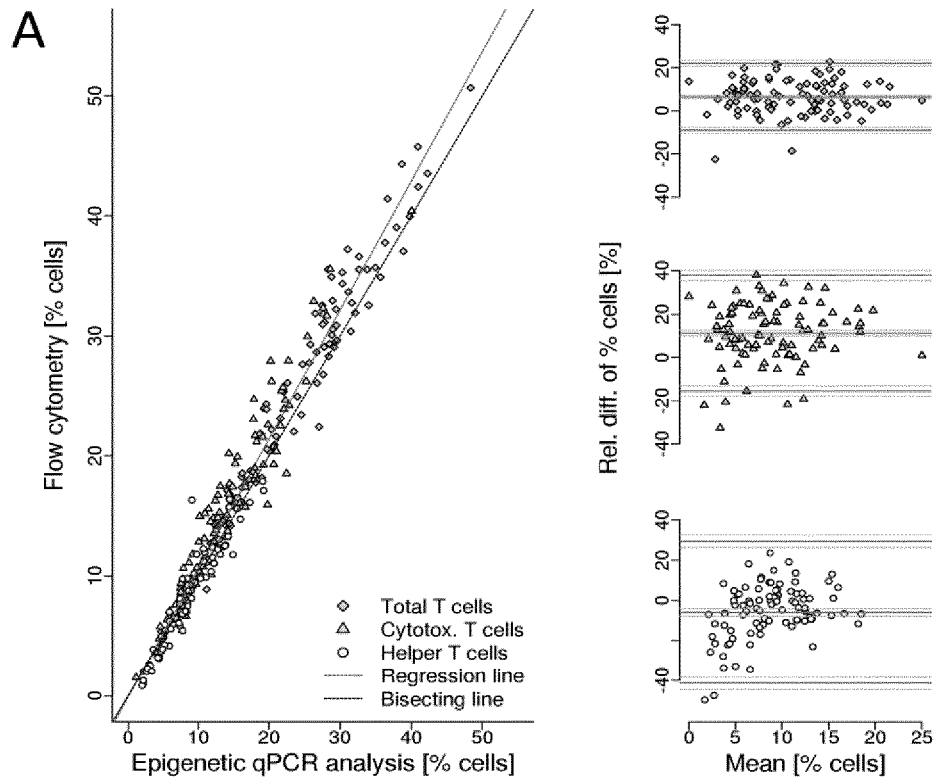
Figure 4:
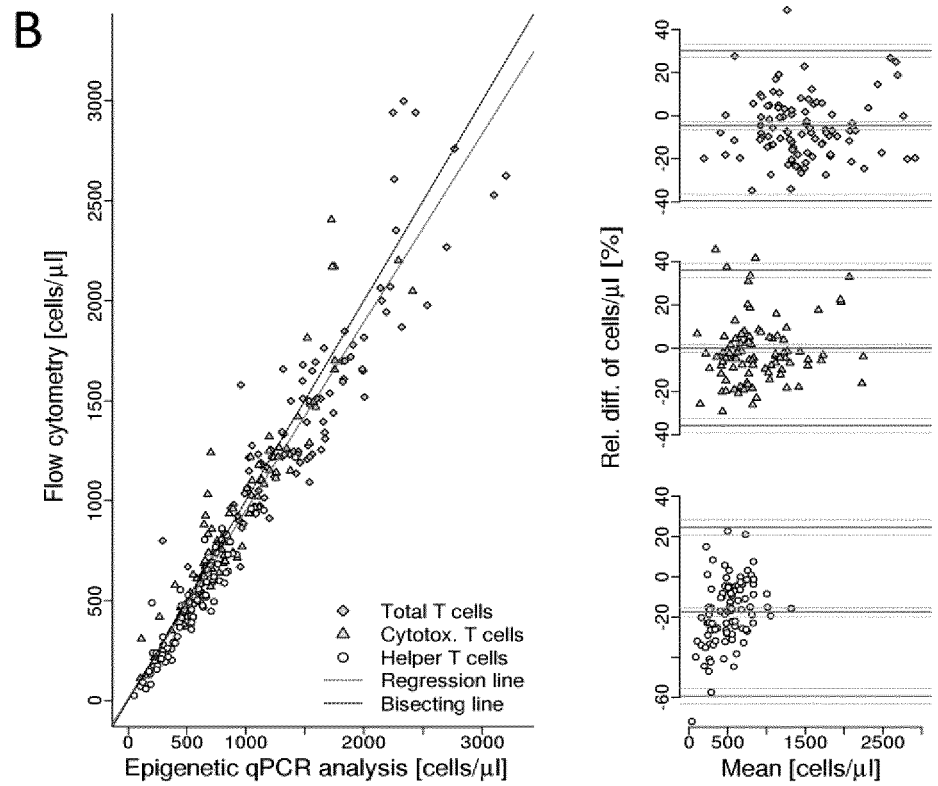

FIG. 4 shows the method comparison between flow cytometry and epigenetic qPCR analysis of T-cell subsets in a HIV cohort. A) illustrates the comparison of relative immune cell counts (as expressed in % related to total nucleated cells). The large graph shows a scatter plot of three T cell populations analyzed via epigenetic qPCR analysis (x-axis) and flow cytometry (y-axis). The lines in black and red represent the bisectrix and the regression line, respectively. Linear correlation coefficient according to Pearson was r=0.982 (p<0.0001). The small graphs display a Bland-Altman analysis where the mean cell count (in %) as averaged between each epigenetic and cytometric measurement (x-axis) was plotted over their (relative) difference (y-axis). In each Bland-Altman plot, the upper and lower red lines reflect the limits of concordance and the central red line illustrates the systematic bias. Above and below each red line, the 95% confidence interval is shown as dotted grey lines. Upper Bland-Altman panel: Total T cells; bias: 6.43%; lower limit of agreement: −9.15%; upper limit of agreement: 22.02%. Middle panel: Cytotoxic T cells; bias: 11.23%; lower limit of agreement: −15.36%; upper limit of agreement: 37.83%. Bottom right: Helper T cells; bias: −6.04%; lower limit of agreement: −41.34%; upper limit of agreement: 29.25%. B) shows the comparison of absolute immune cell counts (as expressed in cells per µl blood). Left side: Scatter plot analysis; Pearson r=0.955 (p<0.0001). Right side: Bland-Altman analysis: Upper panel: Total T cells; bias: −4.76%; lower limit of agreement: −39.62%; upper limit of agreement: 30.09%. Middle panel: Cytotoxic T cells; bias: 0.03%; lower limit of agreement: −35.78%; upper limit of agreement: 35.83%. Bottom right: Helper T cells; bias: −17.61%; lower limit of agreement: −59.68%; upper limit of agreement: 24.46%.

Figure 5:
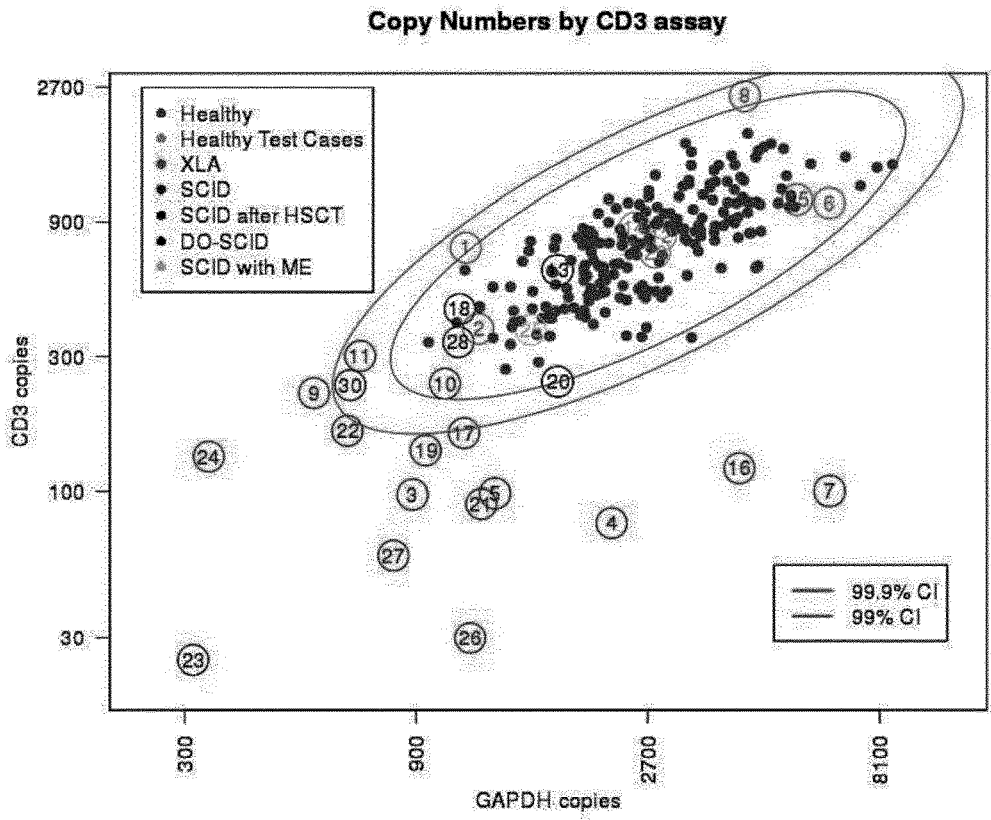
Figure 5:
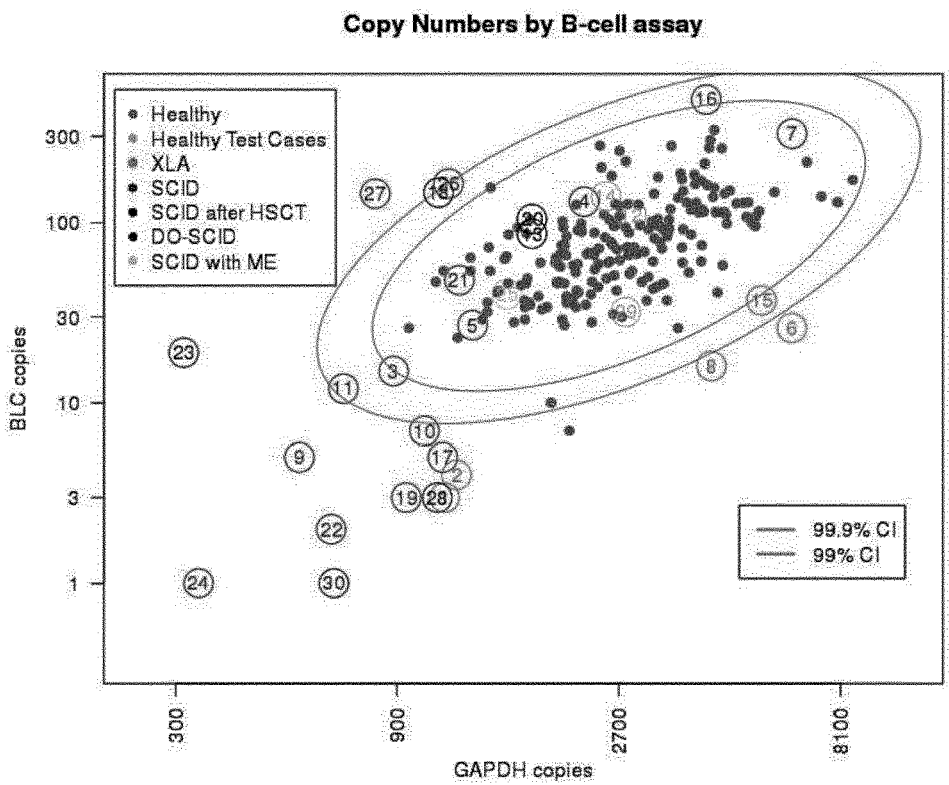
Figure 5:
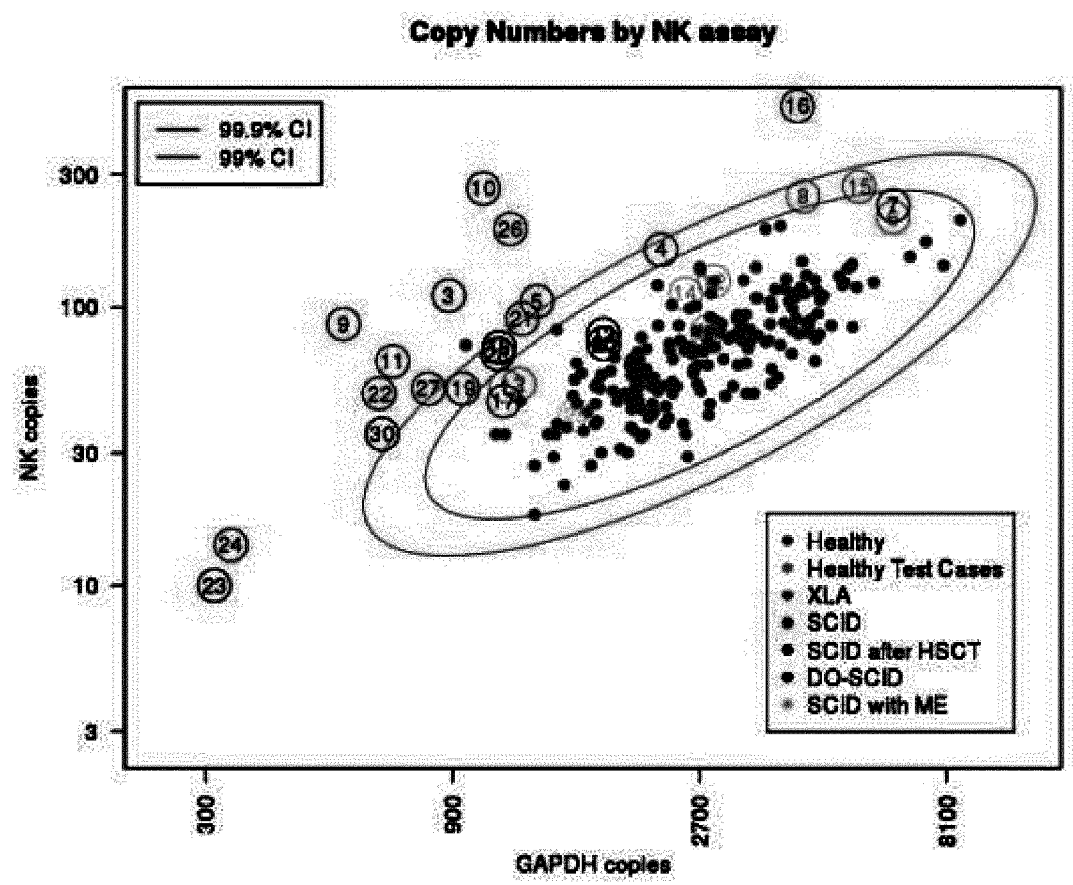

FIG. 5 shows the analysis of control Guthrie cards and PID cases with epigenetic markers for CD3+ T cells, CD19+ B cells, CD56+ NK cells (as well as CD4 and CD8 T cells below). Healthy controls are given in grey dots and 99% (blue) and 99.9% (red) confidence intervals of a bivariate normal distribution are estimated from log transformed copy numbers. Measurement data of the test cohort are given as numbers and color-coded according to phenotype.

EXAMPLES

Abbreviations: Amp, amplicon; qPCR, quantitative real time polymerase chain reaction; FCM, flow cytometry; HSCT, hematopoietic stem cell transplantation. $RD_{ls}$, locus-specific relative demethylation; $RD_u$, universal relative demethylation; $DD_u$, universal definitive demethylation; LC, leukocyte count; CF, conversion factor.

Leukocyte populations. Peripheral blood samples were obtained from healthy donors and fractionated into CD15+ granulocytes, CD14+ monocytes, CD56+ natural killer cells, CD19+ B-lymphocytes, CD3+CD4+ T-helper cells and CD3+CD8+ cytotoxic T cells by high-speed fluorescence activated cell sorting as described previously (16). Purities of sorted cells were >97% as determined by flow cytometry and viability was >99%.

Peripheral whole blood samples. EDTA-anticoagulated peripheral blood samples were collected from 25 healthy subjects from each one blood draw, 97 HIV+ patients under treatment (each one blood draw) in a German outpatient clinic and 26 patients with (acute myeloid) leukemia from San Raffaele University Hospital receiving hematopoietic stem cell transplantation. From the latter cohort 92 blood draws from conditioning phase to 180 days post transplantation were made. All samples were subjected in parallel to epigenetic qPCR analysis and to standard flow cytometry analysis for immune cell quantification (see below) without need for additional venipuncture according to Medical device act. Ethical consent was given at the according institutions. For epigenetic analysis, all data were blinded to experimenters. For diagnostic FACS analysis, samples were not blinded.

DNA preparation. For sequencing and qPCR analysis of purified immune cells, genomic DNA was isolated using DNeasy tissue kit (Qiagen) according to the manufacturer's instructions. In all other applications, blood samples were forwarded to a one-tube lysis and bisulfite conversion without preceding DNA preparation.

Bisulfite conversion. For conversion of purified genomic or plasmid DNA, the EpiTect Fast Bisulfite Conversion Kit (Qiagen) was used following the manufactures protocol. For direct bisulfite conversion of whole blood, 20 µl of EDTA anti-coagulated blood (or calibrator plasmid) was mixed with 16 µl lysis buffer, 3 µl proteinase K (Qiagen) and, where appropriate, 1 µl of $GAP^{[GC]}$ spiker plasmid yielding 20,000 copies/µl blood followed by incubation at 59° C. for 10 minutes. For conversion, 90 µl ammonium bisulfite (68-72%, pH 4.8-5.3, Chemos AG) and 30 µl tetrahydrofurfuryl alcohol (Sigma-Aldrich) were added. Conversion and purification of converted DNA was carried out according to the "EpiTect Fast Bisulfite Conversion Kit" protocol.

Bisulfite sequencing. PCR-amplification was performed in a final volume of 25 µl containing 1×PCR Buffer, 1U Taq DNA polymerase (Qiagen), 200 µM dNTPs, 12.5 pmol each of forward and reverse primers, and approx. 10 ng of bisulfite-converted genomic DNA at 95° C. for 15 minutes and 40 cycles of 95° C. for 1 minute, 55° C. for 45 seconds and 72° C. for 1 minute and a final extension step of 10 minutes at 72° C. PCR products were purified using ExoSAP-IT (USB Corp.) and sequenced applying one PCR primer applying ABI Big Dye Terminator v1.1-chemistry (Applied Biosystems) followed by capillary electrophoresis on an ABI 3100 genetic analyzer. AB1 files were interpreted using ESME (18).

Epigenetic qPCR analysis. Experiments were performed in a final volume of 10 µl using Roche LightCycler 480 Probes Master chemistry containing 50 ng lambda-phage DNA (New England Biolabs) and up to 100 ng converted DNA template or an adequate amount of plasmid. Standard concentration for each primer was at 1.5 µM, except for genomic spiker plasmid (0.75 µM). CD4+ T cell TpG assay (4.5 µM forward; 3 µM reverse primer). Standard probe concentration was at 0.25 µM except for CD4+ T cells, CD8+ T cells, NK cells and spiker plasmid (each 0.125 µM probe for TpG-specific systems). The thermal profile was 95° C. for 10 minutes followed by 50 cycles at 95° C. for 15 seconds and 61° C. for 1 minute.

Plasmids. Two bisulfite-converted sequences corresponding to either the methylated or the demethylated marker regions were designed in silico, synthesized and inserted into plasmid pUC57 (Genscript Inc.) and used as positive control for assay establishment and as quantification standard for qPCR experiments. Standard plasmids harbour all assay target sequences (as TpG- or CpG-variants) and are intra-molecularly linked providing for equimolarity of all assay targets. Plasmids were spectrophotometrically quantified, linearized by Sca I and serially diluted in 10 ng/µl of lambda-phage DNA (New England Biolabs) to obtain quantification standards with 31250, 6250, 1250, 250, 50 or 30 copies per reaction. For qPCR normalization, a single calibrator plasmid was generated harbouring all assay target sequences equimolarly in the genomic unconverted demethylated version. For leukocyte quantification per µl blood, a spike-in plasmid was designed and generated carrying an unconverted artificial GAPDH gene region, which is exactly equivalent to the target of the GAPDH-specific qPCR assay but has all CpG dinucleotides inverted to GpCs ($GAP^{[GC]}$).

Oligonucleotides. Forward (fp), reverse (rp) primers and hydrolysis probes (p) (Metabion AG) are indicated by their chromosomal positions with respect to the human genome assembly GRCh38.p5, Release 84 (March 2016). Oligonucleotides for bisulfite sequencing: AMP1255: fp: 12:6790192-214, rp: 12:6790582-603; AMP1730: fp: 9:128149251-72, rp: 9:128149589-609; AMP2000: fp: 12:6790724-46, rp: 12:6791160-80; AMP2001: fp: 12:6791141-62, rp 12:6791535-60; AMP2007: fp: 2:86821232-54, rp 2:86821674-95; AMP2178: fp: 6:161375641-62, rp 6:161376086-108; AMP2249: fp: 11:68371460-81, rp: 11:68371926-47; AMP2674: fp: 16:88653882-902, rp: 16:88654299-88654320. Oligonucleotides for qPCR analysis: CD4: TpG: fp: 12:6790871-98, rp: 12:6791046-73, p: 12:6790998-1019; CpG: fp: 12:6790871-900, rp: 12:6791046-72, p: 12:6790997-1020. CD8B: TpG: fp: 2:86821374-1400, rp: 2:86821476-93, p: 2:86821425-52; CpG: fp: 2:86821372-1401, rp: 2:86821463-83, p:

2:86821425-55. LPRS: TpG: fp: 11:68371608-28, rp: 11:68371721-45, p: 11:68371666-84; CpG: fp: 11:68371611-35, rp: 11:68371720-48, p: 11:68371662-86. MVD: TpG: fp: 16:88654112-36, rp: 16:88654173-90, p: 16:88654136-55; CpG: fp: 16:88654111-36, rp: 16:88654172-89, p: 16:88654136-58. PARK2: TpG: fp: 6:161375730-55, rp: 6:161375851-66, p: 6:161375804-25; CpG: fp: 6:161375784-807, rp: 6:161375851-70, p: 6:161375805-830. LCN2: TpG: fp: 9:128149258-78, rp: 9:128149353-75, p: 9:128149289-309; CpG: fp: 9:128149257-77, rp: 9:128149353-76, p: 9:128149287-309. Oligonucleotides of the $CD3^+$ T cell and GAPDH-specific amplicons and qPCR-systems have been published previously (15).

Flow cytometric characterization of whole blood samples—To compare results of the epigenic analyses to standard flow cytometry, the absolute number of $CD45^+$ leukocytes was determined after lysis of erythrocytes by a MACSQuant cytometer (Milteny Biotec, Bergisch Gladbach). In addition frequencies and absolute counts of $CD15^+$ granulocytes, $CD14^+$ monocytes, $CD19^+$ B-cells, $CD56^+$ NK cells, total $CD3^+$T cells and $CD4^+$ and $CD8^+$ subsets were calculated as previously described (14,32).

Statistical analysis—CP ("crossing point") of aggregated triplicate measurements was computed by the second-derivative maximum method applying the LC480 software (Roche) to yield copy numbers ("plasmid units") by interpolation (f–1) of amplification (f) from calibration curves generated with dilutions of plasmid-based standards. Method comparison between flow cytometric and qPCR based measuring technique was done as follows: Bivariate data from the two methods were drawn in a scatterplot. Linear Regression was performed testing a) for a slope different from 1 and b) an intercept different from 0. Bland-Altman plots were inspected analyzing bias and precision statistics (28). Acceptable precision was regarded as average deviation from the bias in percent, reflecting the in house limit on the coefficient of variation for intra assay performance, i.e., 0.2. This translates into acceptable limits of agreement of 0.4. The inventors report the estimated bias, the precision statistic and the respective 95% confidence intervals. For correlation, Pearson product-moment correlations were used. Rater agreement was evaluated using Cohens-Kappa coefficient (19). All p-values are two-sided. Statistics software R 3.3.0 was employed.

Cell type-specific bisulfite-conversion. Methylation-dependent conversion of CpG-dinucleotides was analyzed by bisulfite sequencing (18) aiming at marker identification for immune cell populations sorted from human peripheral blood. Candidate loci were selected from the literature or from a genome-wide discovery experiment. As a likely marker for $CD4^+$ T helper cells, the inventors designed three amplicons (Amp) for bisulfite sequence analysis covering regulatory elements within the 5' region of the first intron (Amps 1255, 2000 and 2001) in the CD4 gene. Unmethylated CpG-sites are detected as TpG residues after bisulfite-conversion and amplification exclusively in the target cells, i.e., $CD3^+CD4^+$ T lymphocytes. The same CpGs were inert to bisulfite-conversion in control cell types, including $CD56^+$ natural killer (NK) cells, $CD3^+CD8^+$ T lymphocytes, $CD14^+$ Monocytes, $CD19^+$ B-lymphocytes and $CD15^+$ Granulocytes (FIG. 1). The inventors investigated the CD8B gene as a potentially apt epigenetic mark for $CD8^+$ cytotoxic T cells by designing amplicons targeting regulatory elements within its third intron (Amp 2007). Here, bisulfite-mediated conversion of CpGs was observed exclusively in $CD3^+$T $CD8^+$ (target) cells whilst CpGs were inert to conversion in control cell types. Similar to data for $CD8^+$ and $CD4^+$ T cells, the inventors identified epigenetic marks, each uniquely demethylated in the target cell type and fully methylated in the corresponding control leukocyte populations. Amplicons corresponding to genes LRP5 (Amp2249) and MVD (Amp2674), served as epigenetic markers for B cells and NK cells, respectively. The DNA methylation profile of the intergenic CD3G and CD3D region (Amps 1405, 1406 and 1408), which constitutes a marker for $CD3^+$ T cells and the methylation profile of GAPDH (Amp 1570) were published previously (15).

Figure 2A:
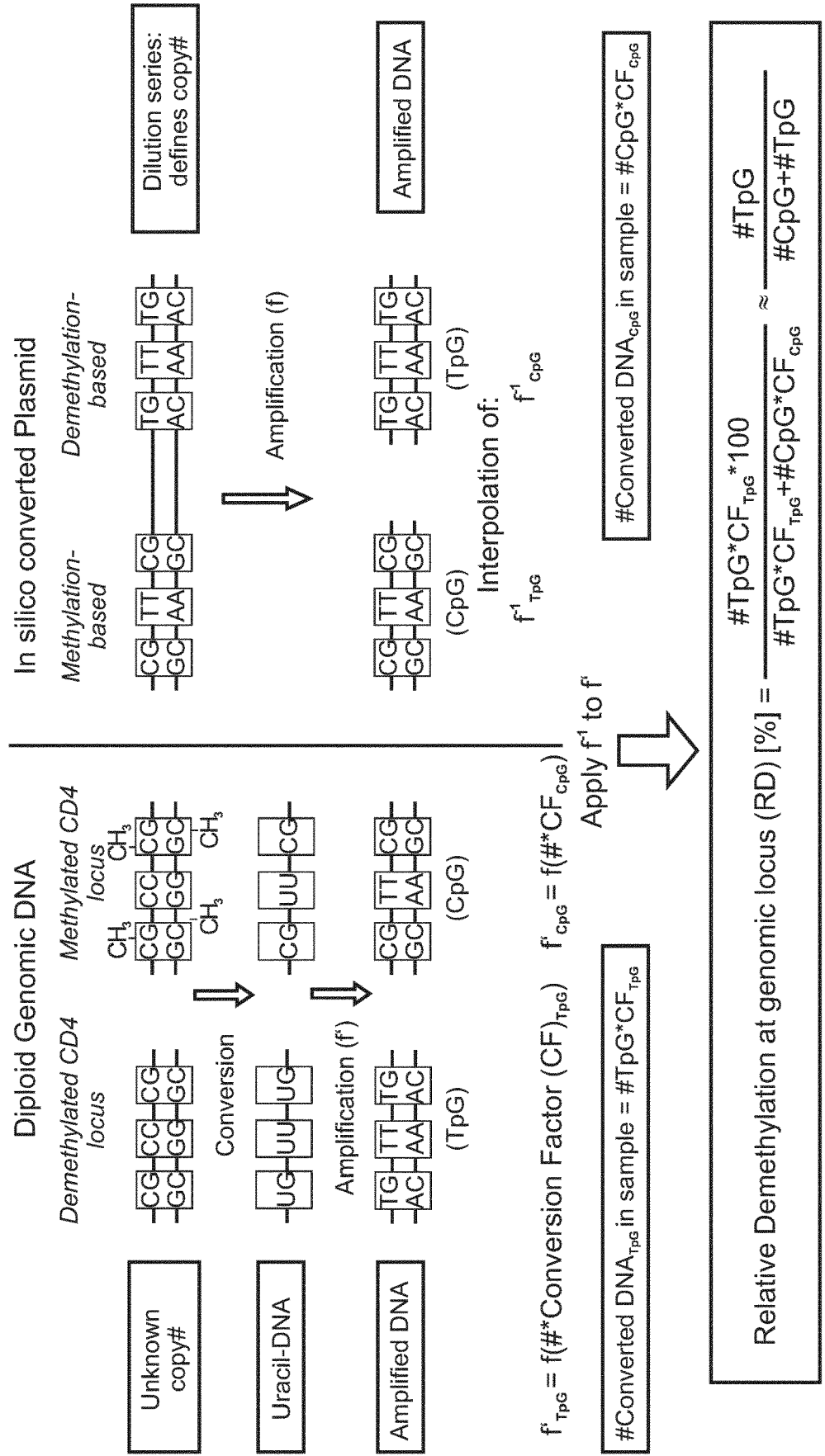
Figure 2B:
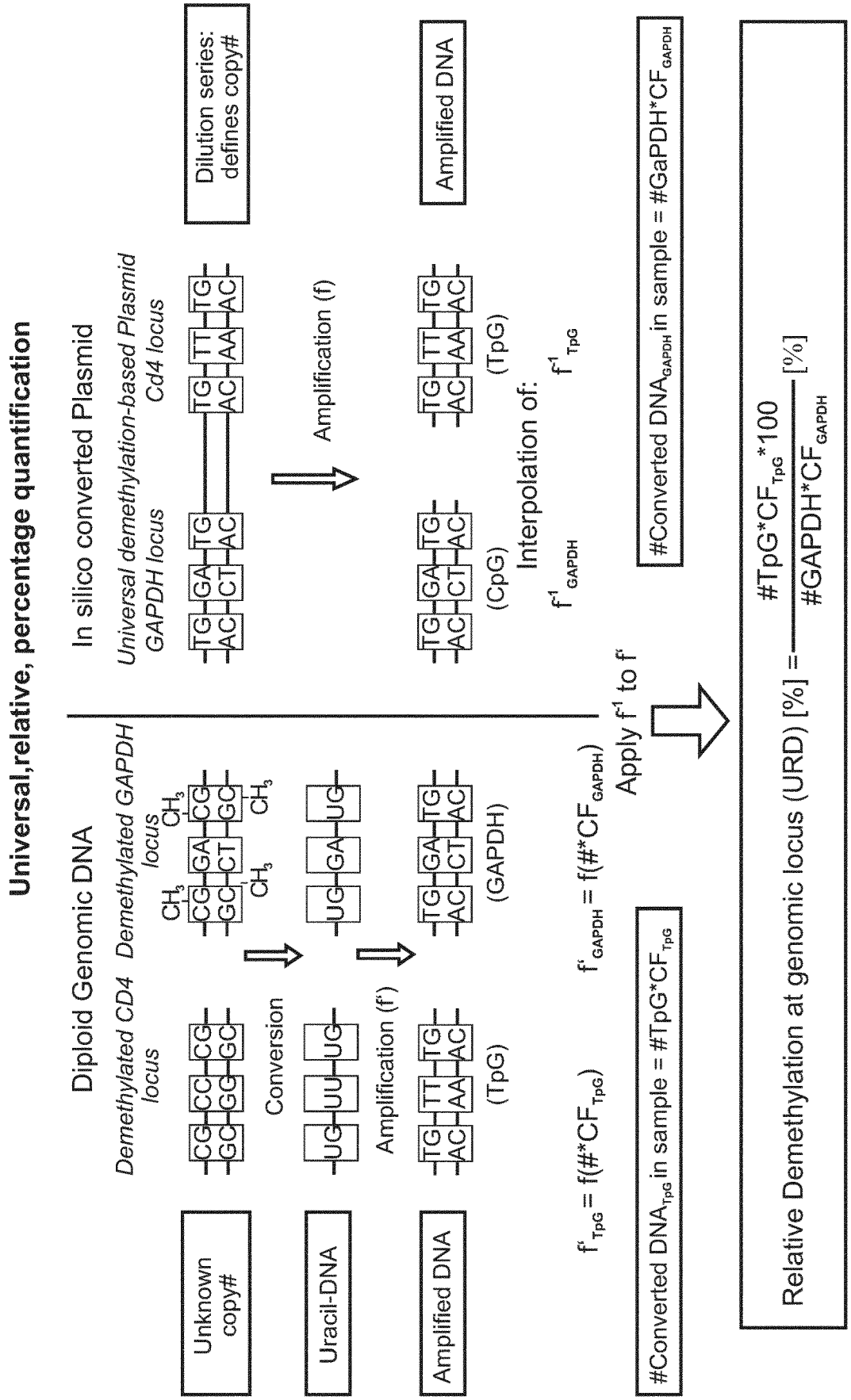

Locus-specific relative qPCR measurements. Targeting the differentially methylated CpG positions described above, quantitative PCR assay systems were designed as described in the method section. The qPCR systems were characterized on in silico bisulfite converted template DNA cloned into plasmids (FIG. 2A, right panel). For the TpG template (mimicking demethylated CpGs in genomic DNA) a universal plasmid carried the target regions for all assay and an artificial $GAP^{[GC]}$ sequence in equimolar stoichiometry (universal TpG-plasmid), whereas the "CpG-plasmids" (mimicking methylated CpGs in genomic DNA) were designed for each amplicon individually. High technical specificity was observed with no cross-reactivity in the mutually antithetic templates (Table 1, "Plasmid-based controls"). The original copy number of the gene sequences in blood samples was estimated by relating the PCR signals from the according amplification (f) to an amplification (f) of the serially diluted plasmids (FIG. 2A). Biological assay specificity was tested on purified immune cell populations. High and low copy numbers were observed for target cell types in the TpG- and CpG-systems, respectively. Conversely, for control cell types low copy numbers were found in the TpG- and high numbers in the CpG-system. Relative demethylation at the respective gene loci ($RD_{ls}$) ranged from 89.9 to 100% in target cell types and from 0.0% to 3% in controls (Table 1). Exceptions were observed for purified $CD4^+$ T cells showing 8.9% demethylation at the CD8B locus and vice versa (i.e., 9.6% CD4 demethylation in $CD8^+$ T cells).

Figure 2C:
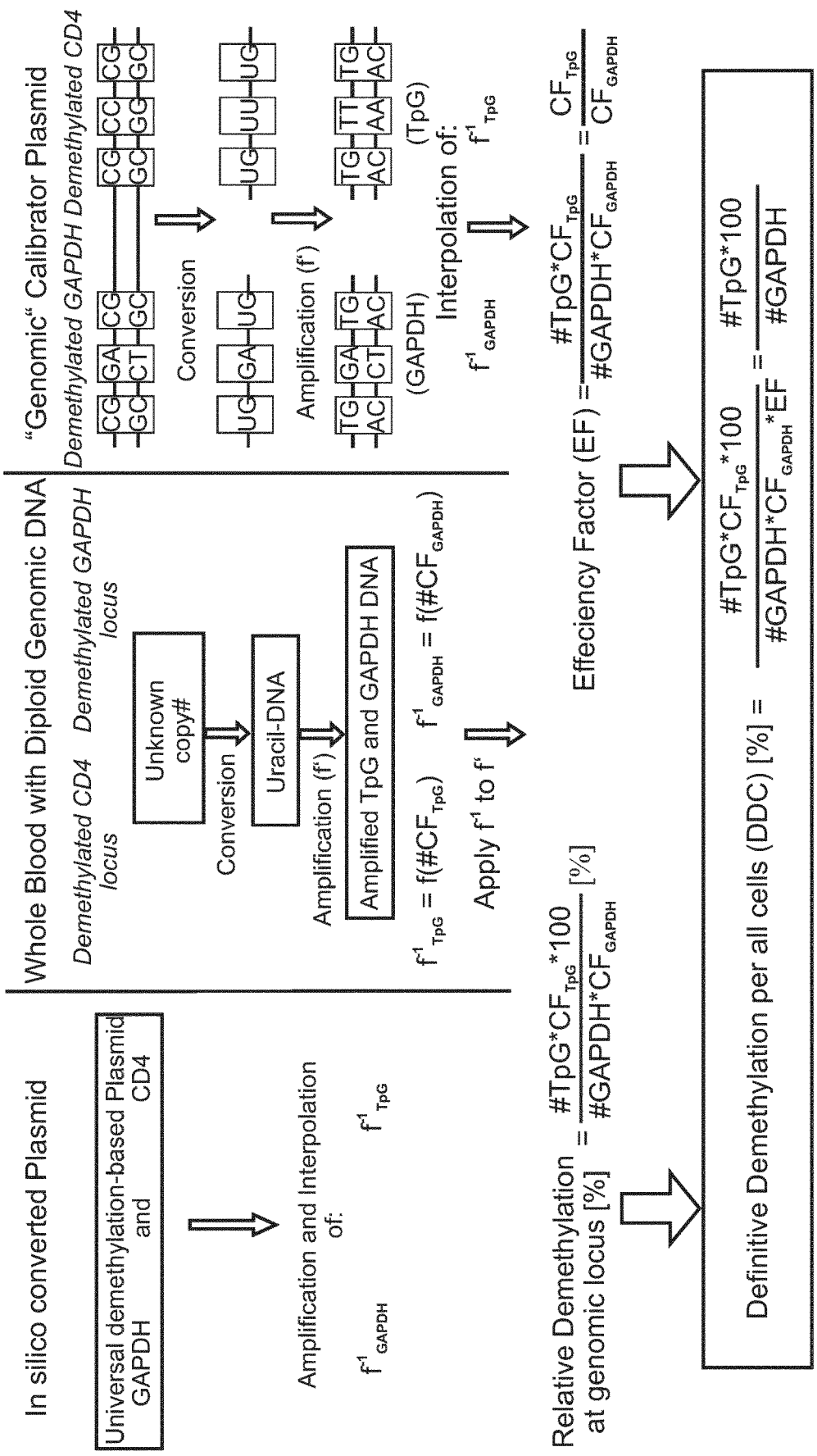

Universal and definitive quantification. To provide a joint basis of quantification for all cells, the demethylated GAPDH-specific amplification was analyzed together with the cell-specific TpG-systems described above (FIG. 2B). The universal TpG-plasmid served as amplification standard. With this, universal relative demethylation ($RD_u$) in samples was determined by relating sample amplification f' to standard amplification (f) for each marker and GAPDH. The inventors' data show that $RD_u$ does not always match with the corresponding locus-specific demethylation ($RD_{ls}$). To compensate for this intrinsic systematic shift a "calibrator plasmid" was adopted harboring all assay targets in equimolar amounts and in their unconverted (i.e., demethylated) state. Efficiency differences between the individual qPCR systems that remained after standard plasmid based normalization were estimated based on the unconverted plasmid and yielded the qPCR efficiency factor (EF). The mean EFs between each cell type specific assay and GAPDH were determined in approx. 25 experiments and ranged between 0.53 for CD4 and 1.17 for CD3x and y (Table 1. EF). Application of EF on the universal relative demethylation ($RD_u$) then allows for universal definitive demethylation quantification ($DD_u$; FIG. 2c).

Figure 2D:
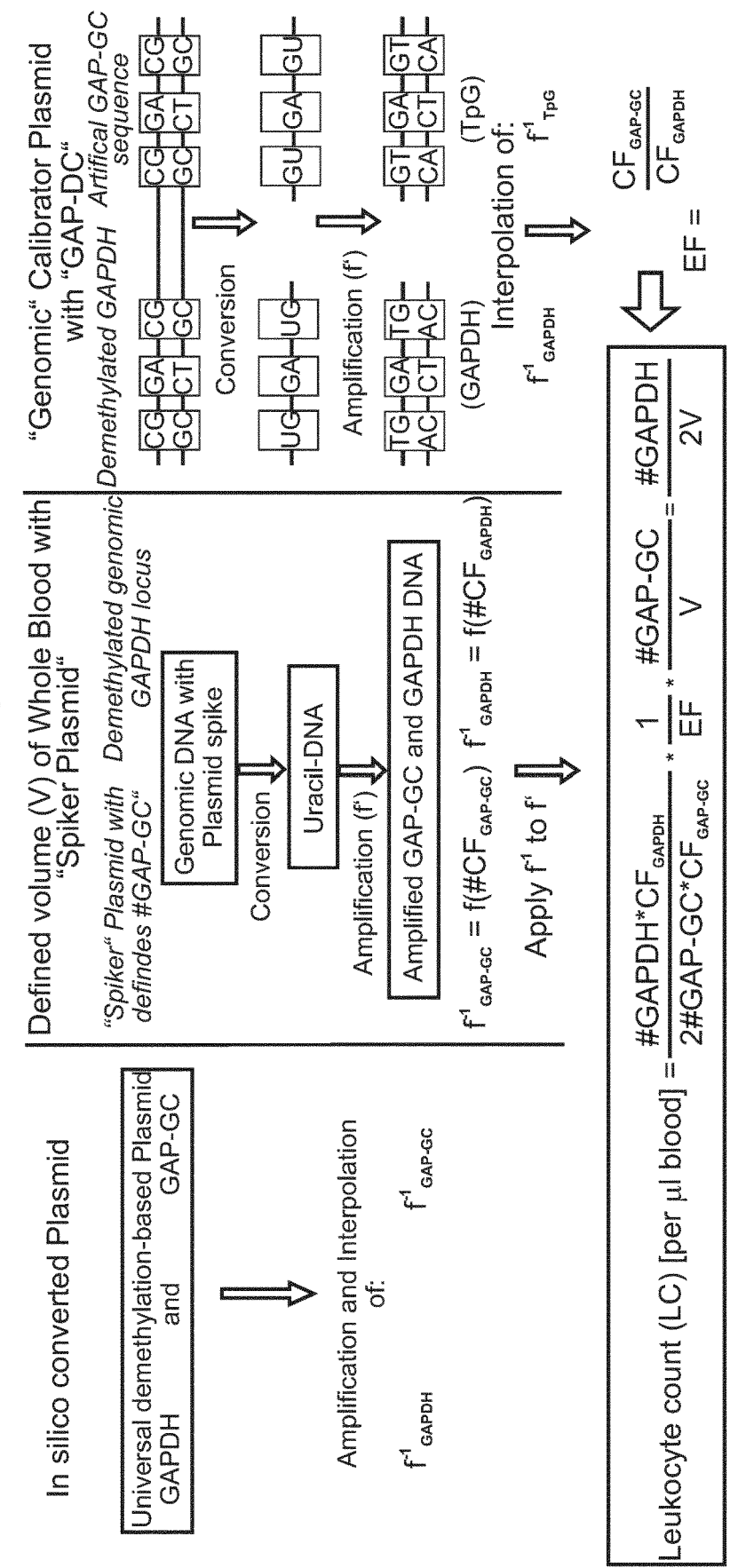

Absolute quantification was established by introducing a "spike-in plasmid" harboring an artificial GAPDH sequence inversing all CpG dinucleotides to GpC ($GAP^{[GC]}$) and an according qPCR assay. Substrate specificity of the $GAP^{[GC]}$- specific qPCR assay was confirmed on bisulfite converted DNA from whole blood with and without spiker plasmid where no cross reactivity with the endogenous GAPDH gene was detected. In contrast, when testing the GAPDH-specific qPCR assay on the spike-in plasmid template harboring an GAP$^{[GC]}$ sequence no amplification signal was detected, too demonstrating a high substrate specificity, which is indispensable for an absolute quantification. For an immune cell counting, the spike-in plasmid was added to blood samples yielding a defined concentration per given initial sample volume (FIG. 2D). In addition, the artificial GAP$^{[GC]}$ sequence was included on the in silico bisulfite converted plasmid standard and the calibrator plasmid yielding the respective equimolarity factor (EF) of 0.87 (GAP$^{[GC]}$; 0.83/0.92) used for correction.

Comparative immune cell counting by flow cytometry and epigenetic qPCR. Blood samples from 25 adult healthy donors were subjected to standard flow cytometry (FCM) and epigenetic qPCR for universal quantification of CD15$^+$ neutrophils, CD14$^+$ monocytes, CD19$^+$ B-cells, CD56$^+$ NK cells, CD3$^+$, CD4$^+$ and CD8$^+$ T-cells. Data from both methods were plotted against each other either as relative (FIG. 3A) or absolute counts (FIG. 3B). Scatter plots indicate for a high level of congruence between both methods with a Pearson correlation coefficient r of 0.95 ($p<0.0001$) for both relative and absolute quantification of leukocyte populations. The regression line comparing FCM and epigenetic qPCR for relative quantification did not significantly deviate from the bisecting line. However, a small but significantly different slope was observed for absolute quantification indicating a proportional systematic bias.

To test the inventors' new approach in a real clinical setting the inventors measured blood samples from 97 HIV$^+$ subjects with respect to quantify CD3$^+$, CD4$^+$ and CD8$^+$ cell counts by standard FCM and epigenetic counting. In this invention, correlation analyses yielded Pearson r correlation coefficients ranging from 0.91 to 0.98 ($p<0.0001$) for relative and absolute quantification (FIG. 4). Absolute quantification was based on the spiking of the GAP$^{[GC]}$ plasmid into the blood samples to determine the overall leukocyte count applying the GAP$^{[GC]}$ specific qPCR assay system. Leukocyte numbers as determined by the FCM and epigenetic qPCR approach were highly correlated (Pearson r=0.8; $p<0.0001$). For the assessment of method comparability the inventors performed Bland-Altman analysis (17; FIG. 4). The systematic difference (bias) between the two methods was below 11% (relative) and 18% (absolute) for all three cell types. Moreover, non-systematic fluctuations remained under 25% for all three markers when comparing FACS to epigenetic qPCR, indicating low levels of imprecision for both approaches. According to these data, biological readouts of FCM and epigenetic counting appeared to be well-correlated for all cell types. Sample collection and preprocessing not always warrants known volumes of blood, e.g., in dried blood spots, barring flow cytometric analysis. To test diagnostic accuracy of epigenetic qPCR in these cases, the inventors determined immune cell counts in Guthrie cards collected from 250 healthy newborns and 30 blood cards from patients with primary immune-deficiencies suffering from SCID (x patients), ADA-SCID (y) and XLA (z). Upon analysis, data were unblinded, results were compared to data obtained with TREC and KREC analysis and the available genetic analysis disclosed. As shown in FIG. 5, 13 out of 15 SCID cases lay out of the 99.9% confidence interval of the normal cohort in the CD3 to GAPDH plot, providing for a positive diagnosis alone. Case No 11 was out of the 99% CI in the B-cell analysis and out of the 99.9% CI in the NK cell analysis. SCID No 10 lay inside the "normal cohort" for the T-cell analysis, but outside the 99.9% CI in both B-cell and NK cell to GAPDH analyses. These combinations in SCID cases No 10 and 11 clearly indicating a severe alteration in the immune cell homeostatis and would require a thorough post-screening analysis. When analyzing delayed onset SCID cases, No 23 was out of the 99.9% interval, No 30 out of the 99% CI and case No. 28 appeared to be unsuspicious in the T-cell analysis. All three cases, however, were detected outside the 99.9% CI in the B-cell analysis and were at least outside the 99% CI in NK cell counts. T cell levels in XLA patients were reported outside the 99% CI for cases No 1 and 8, but all 5 cases were outside the 99% CI in B-cells with No. 1, 2, 6 and 8 outside the 99.9% CI. Also, cases 8 and 15 were outside the 99% CI for NK cells. Case No 15 was outside the 99% CI in the B-cell analysis. Healthy controls (No 12, 14 and 29) that were spiked into the tests invention were within 99% CI in all assays and control samples from patients who had previously received stem cell transplantation (No 13, 18, 20) were inside the 99% CI for T cells, but No 18 still identifies as "non-normal". A SCID case with significant maternal engraftment is not identified in this analysis, as it appears completely unsuspicious in all analyzed markers. Finally, the analysis of CD4 and CD8 cell fractions support the findings of the CD3 marker, but do not show a significant individual added value compared to the CD3 screening. The joint analysis of the GAPDH, CD3, B-Cell and NK cell assay appears to provide information for an accurate diagnosis. As the each of the three panels is tuned to a 99% or (99.9%) CI the inventors need to correct for multiplicity and obtain via Bonferroni Correction a control of the family-wise-error-rate (a generalization of the type I error) at a level of 3% (0.3%).

TABLE 1

| Cell type specificity | Target gene of qPCR assay | Amplification system | Quantification mode | Plasmid based control | | | Analyzed immune cell populations | | | | | |
| --- | --- | --- | --- | --- | --- | --- | --- | --- | --- | --- | --- | --- |
| | | | | TpG-variant | CpG-variant | Calibrator | Th cells CD3$^+$ CD4$^+$ | cytot. T cells CD3$^+$ CD8$^+$ | B cells CD19$^+$ | NK cells CD3$^-$ CD56$^+$ | Monocytes CD14$^+$ | Granu-locytes* CD15$^+$ |
| CD4$^+$ T cells | CD4 | TpG-system [#TpG] | | 30100 | 0 | 6443 | 4795 | 244 | 50 | 58 | 57 | 61 |
| | | CpG-system [#CpG] | | 0 | 29650 | | 8 | 2300 | 7990 | 5100 | 3600 | 5335 |
| | | | RD$_{ls}$ [%] | 100 | 0 | | 99.8 | 9.6 | 0.6 | 1.1 | 1.6 | 1.1 |
| | | | RD$_u$ [%] | | | | 53.4 | 2.7 | 0.6 | 0.6 | 0.6 | 0.7 |
| | | | EF | | | 0.53 | | | | | | |
| | | | DD$_u$ [%] | | | | 91.4 | 6.1 | 0.6 | 1.1 | 1.4 | 1.3 |

TABLE 1-continued

| Cell type specificity | Target gene of qPCR assay | Amplification system | Quantification mode | Plasmid based control | | | Analyzed immune cell populations | | | | | |
|---|---|---|---|---|---|---|---|---|---|---|---|---|
| | | | | TpG-variant | CpG-variant | Calibrator | Th cells CD3$^+$ CD4$^+$ | cytot. T cells CD3$^+$ CD8$^+$ | B cells CD19$^+$ | NK cells CD3$^-$ CD56$^+$ | Monocytes CD14$^+$ | Granu-locytes* CD15$^+$ |
| CD8B$^+$ T Cells | CD8B | TpG-system [#TpG] | | 29850 | 0 | 10457 | 622 | 5845 | 51 | 36 | 19 | 37 |
| | | CpG-system [#CpG] | | 0 | 27150 | | 6400 | 608 | 11100 | 7375 | 5720 | 7985 |
| | | | RD$_{ls}$ [%] | 100 | 0 | | 8.9 | 90.6 | 0.5 | 0.5 | 0.3 | 0.5 |
| | | | RD$_u$ [%] | | | | 6.9 | 65.1 | 0.6 | 0.4 | 0.2 | 0.4 |
| | | | EF | | | 0.87 | | | | | | |
| | | | DD$_u$ [%] | | | | 7.3 | 90.6 | 0.4 | 0.4 | 0.3 | 0.5 |
| B cells | LRPS | TpG-system [#TpG] | | 30550 | 0 | 8723 | 2 | 2 | 9970 | 24 | 5 | 1 |
| | | CpG-system [#CpG] | | 0 | 31500 | | 4760 | 3205 | 1125 | 5105 | 3655 | 5790 |
| | | | RD$_{ls}$ [%] | 100 | 0 | | 0.0 | 0.1 | 89.9 | 0.5 | 0.1 | 0.0 |
| | | | RD$_u$ [%] | | | | 0.0 | 0.0 | 111.0 | 0.3 | 0.1 | 0.0 |
| | | | EF | | | 0.72 | | | | | | |
| | | | DD$_u$ [%] | | | | 0.0 | 0.0 | 91.7 | 0.3 | 0.1 | 0.0 |
| NK cells | MVD | TpG-system [#TpG] | | 27750 | 0 | 12400 | 150 | 169 | 170 | 10550 | 95 | 172 |
| | | CpG-system [#CpG] | | 0 | 25750 | | 9585 | 6850 | 16450 | 494 | 7220 | 11200 |
| | | | RD$_{ls}$ [%] | 100 | 0 | | 1.5 | 2.4 | 1.0 | 95.5 | 1.3 | 1.5 |
| | | | RD$_u$ [%] | | | | 1.7 | 1.9 | 1.9 | 117.5 | 1.1 | 1.9 |
| | | | EF | | | 1.03 | | | | | | |
| | | | DD$_u$ [%] | | | | 1.5 | 2.2 | 1.1 | 101.2 | 1.2 | 1.9 |
| CD3$^+$ T cells | CD3 D/G | TpG-system [#TpG] | | 33350 | 0 | 14133 | 12050 | 8320 | 37 | 59 | 23 | 28.8 |
| | | CpG-system [#CpG] | | 0 | 29450 | | 4 | 1 | 13800 | 9505 | 6810 | 9125.0 |
| | | | RD$_{ls}$ [%] | 100 | 0 | | 100.0 | 100.0 | 0.3 | 0.6 | 0.3 | 0.3 |
| | | | RD$_u$ [%] | | | | 122.8 | 112.1 | 0.2 | 0.6 | 0.3 | 0.3 |
| | | | EF | | | 1.17 | | | | | | |
| | | | DD$_u$ [%] | | | | 104.4 | 95.2 | 0.2 | 0.5 | 0.3 | 0.2 |
| Leukocytes | GAPDH | TpG-system [#TpG] | | | | 12050 | 9815 | 7425 | 15100 | 10110 | 7655 | 8980 |

RD$_{ls}$: Relative demethylation (locus specific) in %;
RD$_u$: Relative demethylation (universal) in %;
EF: Efficiency factor;
DD$_u$: Definitive demethylation (universal) in %

REFERENCES AS CITED:

1.) Adan A, et al (2016) Flow cytometry: basic principles and applications. Crit Rev Biotechnol. 14:1-14.
2.) Whitby L, et al. (2015) Current laboratory practices in flow cytometry for the enumeration of CD 4(+) T-lymphocyte subsets. Cytometry B Clin Cytom.; 88(5):305-11
3.) Nebe C T, et al. (2013) Messunsicherheit und Qualitätssicherung im Bereich der Immunphänotypisierung der Lymphozytensubpopulationen im peripheren Blut. J Lab Med 37(5):233-250.
4.) Herzenberg L A, et al. (2006) Interpreting flow cytometry data. Nat. Immunol., 7(7):681-685.
5.) Kverneland A H, et al. (2016) Age and gender leucocytes variances and references values generated using the standardized ONE-Invention protocol. Cytometry A. 89(6): 543-64.
6.) Maecker H T, et al. (2012) Standardizing immunophenotyping for the Human Immunology Project. Nat Rev Immunol. 12(3):191-200.
7.) Maecker H T, McCoy J P Jr; FOCIS (2010) Human Immunophenotyping Consortium, Amos M, et al., A model for harmonizing flow cytometry in clinical trials. Nat Immunol. 11(11):975-8.
8.) WHO (2016). Consolidated guidelines on the use of antiretroviral drugs for treating and preventing HIV infection. Recommendations for a public health approach— Second edition.
9.) European Aids Clinical Society (2015). European Guidelines for treatment of HIV-positive adults in Europe (Version 8.0; June 2016).
10.) Slatter M A, Cant A J (2011) Hematopoietic stem cell transplantation for primary immunodeficiency diseases. Ann N Y Acad Sci. 1238:122-31
11.) Thoma M D, et al. (2012) Peripheral blood lymphocyte and monocyte recovery and survival in acute leukemia postmyelo ablative allogeneic hematopoietic stem cell transplant. Biol Blood Marrow Transplant. 18(4):600-7.
12.) Nina Shah N, et al. (2015) Hematopoietic Stem Cell Transplantation for Multiple Myeloma: Guidelines from the American Society for Blood and Marrow Transplantation. Biol Blood Marrow Transplant 21:1155-66.
13.) Auletta J J and Lazarus H M (2005) Immune restoration following hematopoietic stem cell transplantation: an evolving target. Bone Marrow Transplantation. 35:835-857.
14.) Wieczorek G, et al., (2009) Quantitative DNA methylation analysis of FOXP3 as a new method for counting regulatory T cells in peripheral blood and solid tissue. Cancer Res. 69:599-608.
15.) Sehouli J, et al. (2011) Epigenetic quantification of tumor-infiltrating T-lymphocytes. Epigenetics 6:236-46.
16.) Baron U, et al., (2007) DNA demethylation in the human FOXP3 locus discriminates regulatory T cells from activated FOXP3(+) conventional T cells. Eur J Immunol. 37:2378-2389.
17.) Lee J W, et al., (2006) Fit-for-purpose method development and validation for successful biomarker measurement. Pharm Res. 23(2):312-28. 15.
18.) Lewin J, et al. (2004) Quantitative DNA methylation analysis based on four dye trace data from direct sequencing of PCR amplificates. Bioinformatics 20:3005-12.
19.) Mary L. McHugh (2012) Interrater reliability: the kappa statistic. Biochem Med (Zagreb); 22(3):276-282.
20.) Warnecke P M, Stirzaker C (1997) Detection and measurement of PCR bias in quantitative methylation analysis of bisulphite-treated DNA. Nucleic Acids Res. 25(21): 4422-6.

21.) de Jonge H J M, et al., (2007) Evidence based selection of housekeeping genes. PLoS One. 2(9):e898

22.) Chen D, et al., (1999) Differential reactivity of the rat S100A4(p9Ka) gene to sodium bisulfite is associated with differential levels of the S100A4 (p9Ka) mRNA in rat mammary epithelial cells. J Biol Chem. 274(4):2483-91.

23.) Harrison J, Stirzaker C, Clark S J (1998) Cytosines adjacent to methylated CpG sites can be partially resistant to conversion in genomic bisulfite sequencing leading to methylation artifacts. Anal Biochem. 264(1):129-32

24.) International Human Genome Sequencing Consortium (2001) Initial sequencing and analysis of the human genome. Nature 409: 860-921

25.) Moore, D M, et al. (2006) CD4 percentage is an independent predictor of survival in patients starting antiretroviral therapy with absolute CD4 cell counts between 200 and 350 cells/microL. HIV Med 7:383-388.

26.) Yu L M, Easterbrook P J, Marshall T (1997) Relationship between CD4 count and CD4% in HIV-infected people. Int J Epidemiol. 26(6):1367-72.

27.) Read S J (2001) Recovery efficiencies of nucleic acid extraction kits as measured by quantitative LightCycler™ PCR. Mol Pathol. 54(2): 86-90.

28.) Giavarina D. (2015) Understanding Bland Altman analysis. Biochemia Medica. 25(2):141-51.

29.) Rodriguez W R, Christodoulides N, Floriano P N, Graham S, Mohanty S, Dixon M, Hsiang M, Peter T, Zavahir S, Thior I, Romanovicz D, Bernard B, Goodey A P, Walker B D, McDevitt J T (2005) A microchip CD4 counting method for HIV monitoring in resource-poor settings. PLoS Med 2(7): e182-e182.

30.) Israeli M, Klein T, Herscovici C, Ram R, Shpilberg O, Sredni B and Yeshurun M. (2013) Cellular immune function monitoring after allogeneic haematopoietic cell transplantation: evaluation of a new assay. Clin Exp Immunol. 172(3): 475-482.

31.) Tsikas D (2009) A proposal for comparing methods of quantitative analysis of endogenous compounds in biological systems by using the relative lower limit of quantification (rLLOQ). J Chromatogr B Analyt Technol Biomed Life Sci. 877(23):2244-51.

32.) Boldt A, Borte S, Fricke S, Kentouche K, Emmrich F, Borte M, Kahlenberg F, Sack U (2014) Eight-color immunophenotyping of T-, B-, and NK-cell subpopulations for characterization of chronic immunodeficiencies, Cytometry B Clin Cytom. 86(3):191-206.

The invention claimed is:

1. A method for determining the absolute copy number of an immune cell type per volume of sample, comprising the steps of:
   A) determining blood immune cells (BIC) per volume of the sample by
   a) providing a defined volume of a sample of human blood comprising diploid genomic DNA of blood immune cells;
   b) providing an in silico bisulfite-converted recombinant nucleic acid comprising at least one demethylation standard gene, and a sequence inversing all CpG dinucleotides to GpC of the at least one demethylation standard gene ("standard I"), wherein the demethylation standard gene is selected from a gene expressed in all cells to be detected;
   c) providing a recombinant nucleic acid comprising demethylated genomic sequence of the at least one demethylation standard gene of b), and a sequence inversing all CpG dinucleotides to GpC of the at least one demethylation standard gene of b) ("calibrator I");
   d) providing a recombinant nucleic acid comprising the sequence inversing all CpG dinucleotides to GpC of the at least one demethylation standard gene of b) ("spiker I");
   e) adding a defined amount of said recombinant nucleic acid of d) to the sample of a) ("spiking");
   f) treating said diploid genomic DNA of the cells to be quantitated from a) and the recombinant nucleic acids of c) and d) with bisulfite to convert unmethylated cytosines into uracil;
   g) amplifying of said nucleic acids b), c), and f) using suitable primer pairs to produce at least one amplicon pair selected from the group consisting of AMP1570 with at least one of AMP1255, 2000, 2001, 2007, 2249, 2674, 1405, 1406, and 1408; and
   h) identifying the blood immune cells (BIC) per volume of sample based on analyzing said amplicon pair(s) as produced in step g),
   B) determining a fraction of demethylation per all cells (DDC) in the sample by
   i) providing a sample of human blood comprising diploid genomic DNA of blood cells to be quantitated;
   j) providing an in silico bisulfite-converted recombinant nucleic acid comprising at least one demethylation standard gene, wherein said demethylation standard gene is selected from a gene expressed in all cells to be detected, and at least one blood cell specific gene ("standard II");
   k) providing a recombinant nucleic acid comprising the demethylated genomic sequence of said at least one demethylation standard gene of j), and of said at least one blood cell specific gene of j) ("calibrator II");
   l) treating said diploid genomic DNA of the cells to be quantitated of i) and said recombinant nucleic acid of k) with bisulfite to convert unmethylated cytosines into uracil;
   m) amplifying of said nucleic acids of j), k), and l) using suitable primer pairs to produce at least one amplicon pair selected from the group consisting of AMP1570 with at least one of AMP1255, 2000, 2001, 2007, 2249, 2674, 1405, 1406, and 1408; and
   n) identifying the fraction of demethylation per all cells (DDC) based on analyzing said amplicon pair(s) as produced in step m), and
   C) Multiplying the BIC as identified with the DDC as identified, and thereby determining the absolute copy number of the immune cell type per volume of sample.

2. The method of claim 1, wherein said blood immune cell is selected from a leukocyte, a T-lymphocyte, a granulocyte, a monocyte, a B-lymphocyte and/or an NK-cell.

3. The method of claim 1, wherein said recombinant nucleic acid is selected from a plasmid, a yeast artificial chromosome (YAC), human artificial chromosome (HAC), PI-derived artificial chromosome (PAC), a bacterial artificial chromosome (BAC), and a PCR-product.

4. The method of claim 1, wherein said demethylation standard gene is selected from a gene expressed in all cells to be detected and is a housekeeping gene.

5. The method of claim 1, wherein said blood immune cell specific gene is expressed in all blood immune cells to be detected.

6. The method of claim 3, wherein said blood sample is selected from peripheral blood samples, capillary blood samples, peripheral blood monocytes, blood clots, or dried blood spots.

7. The method of claim 1, further comprising the step of concluding on the immune status of a mammal based on the absolute copy number of the immune cell type per volume of sample as determined.

8. The method of claim 4, wherein the housekeeping gene is GAPDH.

9. The method of claim 5, wherein the gene expressed in all blood immune cells is CD4.

* * * * *